US008153597B2

(12) United States Patent
Stanton et al.

(10) Patent No.: US 8,153,597 B2
(45) Date of Patent: Apr. 10, 2012

(54) MODULATORS OF THE ABC TRANSPORTER FAMILY AND METHODS FOR THEIR USE

(75) Inventors: Bruce Stanton, Hanover, NH (US); George O'Toole, Jr., Hanover, NH (US); Agnieszka Swiateck-Urban, Pittsburgh, PA (US); Daniel P. MacEachran, Orford, NH (US); Sophie Moreau Marquis, Nashua, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 12/712,336

(22) Filed: Feb. 25, 2010

(65) Prior Publication Data

US 2010/0197593 A1    Aug. 5, 2010

Related U.S. Application Data

(60) Division of application No. 11/691,595, filed on Mar. 27, 2007, now abandoned, which is a continuation-in-part of application No. 10/575,577, filed on May 24, 2006, now abandoned, which is a continuation of application No. PCT/US2004/033874, filed on Oct. 14, 2004.

(60) Provisional application No. 60/511,609, filed on Oct. 15, 2003.

(51) Int. Cl.
*A61K 38/16* (2006.01)
*A61K 38/00* (2006.01)

(52) U.S. Cl. .......................................... 514/21.2; 514/1.1

(58) Field of Classification Search .................... None
See application file for complete search history.

(56) References Cited

U.S. PATENT DOCUMENTS

| | | | | |
|---|---|---|---|---|
| 6,329,172 | B1 | 12/2001 | Rhee et al. | 435/69.1 |
| 6,551,795 | B1* | 4/2003 | Rubenfield et al. | 435/69.1 |
| 7,517,849 | B1* | 4/2009 | Tarasova et al. | 514/2 |
| 2003/0064438 | A1 | 4/2003 | Feder et al. | 435/69.1 |
| 2004/0087527 | A1 | 5/2004 | Day et al. | 514/44 |

OTHER PUBLICATIONS

SEQ ID No: 18289 from US Patent No. 6,551,795 from http://segdata.uspto.gov/?pageRequest=viewSequence&DocID=6551795&seqID=18289, pp. 1-2. Accessed May 11, 2009.*
Hancock Rew, Chapple DS; "Peptide Antibiotics," MiniReview, Antimicrobial Agents and Chemotherapy, Jun. 1999, 43(6): 1317-1323.*
Rudinger J, "Characteristics of the amino acids as components of a peptide hormone sequence," Peptide Hormones, J.A. Parsons, Edition, University Park Press, Jun. 1976, pp. 1-7.*
Designing Custom Peptides from SIGMA GENOSYS, from http://www.sigma-genosys.com/peptide_design.asp, pp. 1-2. Accessed Dec. 16, 2004.*
Schinzel R, Drueckes P, "The phosphate recognition site of *Escherichia coli* maltodextrin phosphorylase," FEBSs, Jul. 1991, 286(1,2): 125-128.*
Berendsen HJC, "A Glimpse of the Holy Grail?" Science, Oct. 23, 1998, 282: 642-643.*
Voet D and Voet JG, "Biochemistry" Second Edition, John Wiley & Sons, Inc., 1995, pp. 235-241.*
Ngo JT, Marks J, Karplus M, "Computational Complexity, Protein Structure Prediction, and the Levinthal Paradox," The Protein FOlding PRoblem and Tertiary Structure Prediction, K. Mere, Jr and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," Journal of Molecular Biology, 2002, 324: 373-386.*
GenBank Accession No. Q9HZR3, pp. 1-2. Sequene created Mar. 1, 2001 and updated Mar. 1, 2001. Accessed Nov. 30, 2009.*
Al-Awqati, Qais, "Alternative treatment for secretory diarrhea revealed in a new class of CFTR inhibitors", The Journal of Clinical Investigation 2002 110(11):1599-1601.
Arceci, Robert J., Clinical Significance of P-Glycoprotein in Multidrug Resistance Malignancies, Blood 1993 81(9):2215-2222.
Biedler, Jun. L., "Drug Resistance:Genotype versus Phenotype-Thirty-second G.H. A. Clowes Memorial Award Lecture", Cancer Research 1994 54:666-678.
Broxterman et al., "Multidrug resistance proteins and other drug transport-related resistance to natural product agents", Current Opinion in Oncology 1995 7:532-540.
Cole et al., "Overexpression of a Transporter Gene in a Multidrug-Resistant Human Lung Cancer Cell Line", Science 1992 258:1650-1654.
Dalton et al., "The Multidrug-Resistance Gene (*MDR1*) Represents a Potential Target for Reversing Drug Resistance in Human Malignancies", J. Nih Res. 1994 6:54-58.
Demolombe et al., "ATP-binding cassette proteins as targets for drug discovery", TIPS 1996 17:273-275.
Fojo et al., "Expression of a multidrug-resistance gene in human tumors and tissues", Proc. Natl. Acad. Sci. USA 1987 84:265-269.
Gregorcyk et al., "p-Glycoprotein Expression as a Predictor of Breast Cancer Recurrence", Annals of Surgical Oncology 1996 3(1):8-14.

(Continued)

*Primary Examiner* — Julie Ha
(74) *Attorney, Agent, or Firm* — Licata & Tyrrell P.C.

(57) ABSTRACT

An isolated factor derived from the bacterium *Pseudomonas aeruginosa* and confirmed by proteomics to be a protein that reduces expression of ABC transmembrane proteins and active fragments and mimetics thereof are provided. Also provided is a method for inhibiting expression of ABC transmembrane proteins in cells by administering to the cells the isolated factor or protein or active fragment thereof or a mimetic thereof. Such methods are useful in the enhancing delivery of small molecule therapeutic agents to the CNS and in treating cancers, particularly multidrug resistant cancers, and secretory diarrhea. In addition, compositions, methods for identifying compositions and methods for use of compositions that inhibit suppression of ABC transmembrane protein expression or reduce epoxide hydrolase activity by this factor are provided. Such compositions and methods are useful in treatment of cystic fibrosis.

3 Claims, No Drawings

OTHER PUBLICATIONS

Hamilton et al., "Differential Effects of Chromium (VI) on Constitutive and Inducible Gene Expression in Chick Embryo Liver In Vivo and Correlation With Chromium (VI)-Induced DNA damage", Molecular Carcinogenesis 1989 2:274-286.

Ihnat et al., "Suppression of P-Glycoprotein Expression and Multidrug Resistance by DNA Cross-Linking Agents", Clinical Cancer Research 1997 3:1339-1346.

Kerbel et al., "Multicellular Resistance : A New Paradigm to Explain Aspects of Acquired Drug Resistance of Solid Tumors", Cold Spring Harbor Symp. Quant. Biol. 1994 59:661-672.

Koh et al., "The Value of Immunohistochemical Detection of P-Glycoprotein in Breast Cancer Before and After Induction Chemotherapy", Yonsei Medical Journal 1992 33(2):137-142.

Kunzelmann et al., "Electrolyte Transport in the Mammalian Colon:Mechanisms and Implications for Disease", Physiol. Rev. 2002 82:245-289.

List, A.F., "Role of multidrug resistance and its pharmacological modulation in acute myeloid leukemia", Leukemia 1996 10:937-942.

McCaffrey et al., "Effects of the Genotoxic Carcinogen Chromium (VI) on Basal and Hormone-Inducible Phosphoenolpyruvate Carboxykinase Gene Expression In Vivo:CorrelationWithGlucocorticoid-andDevelopmental-lyRegulatedExpression", Molecular Carcinogenesis 1994 10:189-198.

Merkel et al., "Electrophoretic Analysis of 248 Clinical Breast Cancer Specimens for P-Glycoprotein Overexpression or Gene Amplification", J. Clin. Oncol. 1989 7(8):1129-1136.

Nooter et al., "Clinical Relevance of P-Glycoprotein Expression in Haematological Malignancies", Leukemia Research 1994 18(4):233-243.

Roninson, Igor B., "The Role of the MDR1 (P-Glycoprotein) Gene in Multidrug Resistance In Vitro and In Vivo", Biochemical Pharmacology 1992 43(1):95-102.

Schneider et al., "P-Glycoprotein expression in treated and untreated human breast cancer", Br. J. Cancer 1989 60:815-818.

Demuth et al., "Interaction of *Actinobacillus actinomycetemcomitans* outer membrane vesicles with HL60 cells does not require leukotoxin", Cellular Microbiology 2003 5(2):111-121.

Horstman et al., "Enterotoxigenic *Escherichia coli* Secretes Active Heat-labile Enterotoxin via Outer Membrane Vesicles", J. Biol. Chem. 2000 275(17):12489-12496.

Kesty et al., "Enterotoxigenic *Escherichia coil* vesicles target toxin delivery into mammalian cells", The EMBO Journal 2004 23:4538-4549.

Kuchma et al., "Three-Component Regulatory System Regulates Biofilm Maturation and Type III Secretion in *Pseudomonas aeruginosa*", J. Bacteriology 2005 187(4):1441-1454.

Mashburn et al., "Membrane vesicles traffic signals and facilitate group activities in a prokaryote", Nature 2005 437:422-425.

Maitra et al., "Differential effects of mitomycin C and doxorubicin on P-glycoprotein expression", Biochem. J. 2001 355:617-624.

Shanks et al., "*Saccharomyces cerevisiae*-Based Molecular Tool Kit for Manipulation of Genes from Gram-Negative Bacteria", Applied and Environmental Microbiology 2006 72(7):5027-5036.

Stover et al., "Complete genome sequence of *Pseudomonas aeruginosa* PA01, an opportunistic pathogen", Nature 2000 406:959-964.

Swiatecka-Urban et al., "*Pseudomonas aeruginosa* inhibits endocytic recycling of CFTR in polarized human airway epithelial cells", Am J. Physiol Cell Physiol 2006 290:C862-C872.

Vandorpe et al., "CFTR mediates electrogenic chloride secretion in mouse inner medullary collecting duct (mIMCD-K2) cells", Am J. Physiol. Cell Physiol. 1995 269(38):C683-C689.

Worlitzsch et al., "Effects of reduced mucus oxygen concentration in airway *Pseudomonas* infections of cystic fibrosis patients", J. Clinical Investigation 2002 109(3):317-325.

NCBI Accession No. AE004091 [gi:110227054] with Revision History—Aug. 30, 2000—Jul. 7, 2006.

* cited by examiner

SEQUENCE LISTING

<160> NUMBER OF SEQ ID NOS: 23

<210> SEQ ID NO 1
<211> LENGTH: 319

<212> TYPE: PRT
<213> ORGANISM: Pseudomonas aeruginosa

<400> SEQUENCE: 1

```
Met Ile Leu Asp Arg Leu Cys Arg Gly Leu Leu Ala Gly Ile Ala Leu
 1               5                  10                  15
Thr Phe Ser Leu Gly Gly Phe Ala Ala Glu Glu Phe Pro Val Pro Asn
            20                  25                  30
Gly Phe Glu Ser Ala Tyr Arg Glu Val Asp Gly Val Lys Leu His Tyr
        35                  40                  45
Val Lys Gly Gly Gln Gly Pro Leu Val Met Leu Val His Gly Phe Gly
 50                  55                  60
Gln Thr Trp Tyr Glu Trp His Gln Leu Met Pro Glu Leu Ala Lys Arg
 65                  70                  75                  80
Phe Thr Val Ile Ala Pro Asp Leu Pro Gly Leu Gly Gln Ser Glu Pro
                 85                  90                  95
Pro Lys Thr Gly Tyr Ser Gly Glu Gln Val Ala Val Tyr Leu His Lys
            100                 105                 110
Leu Ala Arg Gln Phe Ser Pro Asp Arg Pro Phe Asp Leu Val Ala His
        115                 120                 125
Asp Ile Gly Ile Trp Asn Thr Tyr Pro Met Val Val Lys Asn Gln Ala
130                 135                 140
Asp Ile Ala Arg Leu Val Tyr Met Glu Ala Pro Ile Pro Asp Ala Arg
145                 150                 155                 160
Ile Tyr Arg Phe Pro Ala Phe Thr Ala Gln Gly Glu Ser Leu Val Trp
                165                 170                 175
His Phe Ser Phe Phe Ala Ala Asp Asp Arg Leu Ala Glu Thr Leu Ile
            180                 185                 190
Ala Gly Lys Glu Arg Phe Phe Leu Glu His Phe Ile Lys Ser His Ser
        195                 200                 205
Ser Asn Thr Glu Val Phe Ser Glu Arg Leu Leu Asp Leu Tyr Ala Arg
    210                 215                 220
Ser Tyr Ala Lys Pro His Ser Leu Asn Ala Ser Phe Glu Tyr Tyr Arg
225                 230                 235                 240
Ala Leu Asn Glu Ser Val Arg Gln Asn Ala Glu Leu Ala Lys Thr Arg
                245                 250                 255
Leu Gln Met Pro Thr Met Thr Leu Ala Gly Gly His Gly Gly Met
            260                 265                 270
Gly Thr Phe Gln Leu Glu Gln Met Lys Ala Tyr Ala Asp Asp Val Glu
        275                 280                 285
Gly His Val Leu Pro Gly Cys Gly His Trp Leu Pro Glu Glu Cys Ala
    290                 295                 300
Ala Pro Met Asn Arg Leu Val Ile Asp Phe Leu Ser Arg Gly Arg
305                 310                 315
```

<210> SEQ ID NO 2
<211> LENGTH: 960
<212> TYPE: DNA
<213> ORGANISM: Pseudomonas aeruginosa

<400> SEQUENCE: 2

```
atgatcctcg atagactctg ccgcggcctc ctggccggca tcgccctgac cttctccctg    60
ggcggcttcg ccgccgagga attccccgtc ccgaatggct cgaaagcgc ctaccgggaa   120
gtcgacggcg tgaagctgca ctacgtgaaa ggcggccagg gccgctggt gatgctggta   180
cacggtttcg gccagaccct ggtacgaatgg caccaactga tgccggaact ggccaagcgc   240
```
ttcaccgtga tcgcgccgga cctgcccggc ctcggccagt ccgagccgcc gaagaccggc    300
tatagcggcg aacaggtcgc cgtctacctg cacaagctgg cccggcaatt cagcccggat    360
cgcccgttcg acctggtggc ccacgacatc ggtatctgga acacctaccc gatggtggtg    420
aagaaccagg ccgacatcgc ccgcctggtg tacatggaag cgccgatccc ggacgcgcgg    480
atctaccgct tcccggcctt caccgcccag ggcgagtcgc tggtctggca cttcagtttc    540
ttcgccgccg acgaccgcct ggcggaaacc ctgattgccg gcaaggaacg cttcttcctc    600
gagcacttca tcaagtccca ttccagcaac accgaggtgt tcagcgagcg cctgctggat    660
ctgtacgcca ggtcgtacgc caagccgcac agcctgaacg cctcgttcga gtactaccgc    720
gcgttgaacg agagcgtgcg gcagaacgcc gaactggcga agacccgcct gcagatgcca    780
accatgaccc tcgccggcgg cggccacggc ggcatgggca cgttccagct ggagcagatg    840
aaagcctatg cggacgacgt cgaaggccat gtcctgcccg gctgcggcca ctggctgccg    900
gaagagtgcg ccgcgccgat gaatcgcctg gtgatcgact cctcagccg cggtcgctga    960

<210> SEQ ID NO 3
<211> LENGTH: 28
<212> TYPE: DNA
<213> ORGANISM: Artificial sequence
<220> FEATURE:
<223> OTHER INFORMATION: Synthetic

<400> SEQUENCE: 3
gaggaattcc ccgtcccgaa tggcttcg                                        28

<210> SEQ ID NO 4
<211> LENGTH: 36
<212> TYPE: DNA
<213> ORGANISM: Artificial sequence
<220> FEATURE:
<223> OTHER INFORMATION: Synthetic

<400> SEQUENCE: 4
ccgcggatcc gccagaccag cgactcgccc tgggcg                               36

<210> SEQ ID NO 5
<211> LENGTH: 38
<212> TYPE: DNA
<213> ORGANISM: Artificial sequence
<220> FEATURE:
<223> OTHER INFORMATION: Synthetic

<400> SEQUENCE: 5
ccgcggatcc gtcctgggtc tgtgcgccct ggtactgg                             38

<210> SEQ ID NO 6
<211> LENGTH: 36
<212> TYPE: DNA
<213> ORGANISM: Artificial sequence
<220> FEATURE:
<223> OTHER INFORMATION: Synthetic

<400> SEQUENCE: 6
ccgcgaattc cgcgccgacc gcgctgagcg acagcg                               36

<210> SEQ ID NO 7
<211> LENGTH: 35
<212> TYPE: DNA
<213> ORGANISM: Artificial sequence
<220> FEATURE:
<223> OTHER INFORMATION: Synthetic -continued

<400> SEQUENCE: 7
cgccggatcc ggcctggcgc tgacacccgc ggccc                                35

<210> SEQ ID NO 8
<211> LENGTH: 35
<212> TYPE: DNA
<213> ORGANISM: Artificial sequence
<220> FEATURE:
<223> OTHER INFORMATION: Synthetic

<400> SEQUENCE: 8
ccgcgaattc gcactgccgc gaatggtcgc cgcgg                                35

<210> SEQ ID NO 9
<211> LENGTH: 67
<212> TYPE: DNA
<213> ORGANISM: Artificial sequence
<220> FEATURE:
<223> OTHER INFORMATION: Synthetic

<400> SEQUENCE: 9
gggttttccc agtcacgacg ttgtaaaacg acggccagtg cccgcaagcg gctgttcgtc    60
gcctgcc                                                              67

<210> SEQ ID NO 10
<211> LENGTH: 46
<212> TYPE: DNA
<213> ORGANISM: Artificial sequence
<220> FEATURE:
<223> OTHER INFORMATION: Synthetic

<400> SEQUENCE: 10
ctgatcgccc ggaccgggac gacggttgtg cttccttggt ggggtc                   46

<210> SEQ ID NO 11
<211> LENGTH: 46
<212> TYPE: DNA
<213> ORGANISM: Artificial sequence
<220> FEATURE:
<223> OTHER INFORMATION: Synthetic

<400> SEQUENCE: 11
gaccccacca aggaagcaca accgtcgtcc cggtccgggc gatcag                   46

<210> SEQ ID NO 12
<211> LENGTH: 64
<212> TYPE: DNA
<213> ORGANISM: Artificial sequence
<220> FEATURE:
<223> OTHER INFORMATION: Synthetic

<400> SEQUENCE: 12
gtgagcggat aacaatttca cacaggaaac agctatgacc cgaacagcgc ggtgtccttg    60
aagc                                                                 64

<210> SEQ ID NO 13
<211> LENGTH: 33
<212> TYPE: DNA
<213> ORGANISM: Artificial sequence
<220> FEATURE:
<223> OTHER INFORMATION: Synthetic

<400> SEQUENCE: 13
ccgcgctagc ccaaggaagc acaaccatga tcc                                 33

<210> SEQ ID NO 14
<211> LENGTH: 32
<212> TYPE: DNA
<213> ORGANISM: Artificial sequence
<220> FEATURE:
<223> OTHER INFORMATION: Synthetic

<400> SEQUENCE: 14
ccgcggtacc tcagcgaccg cggctgagga ag            32

<210> SEQ ID NO 15
<211> LENGTH: 83
<212> TYPE: DNA
<213> ORGANISM: Artificial sequence
<220> FEATURE:
<223> OTHER INFORMATION: Synthetic

<400> SEQUENCE: 15
gtatcaggct gaaaatcttc tctcatccgc tcaatgatg atgatgatga tggcgaccgc     60
ggctgaggaa gtcgatcacc agg            83

<210> SEQ ID NO 16
<211> LENGTH: 65
<212> TYPE: DNA
<213> ORGANISM: Artificial sequence
<220> FEATURE:
<223> OTHER INFORMATION: Synthetic

<400> SEQUENCE: 16
gatttaatct gtatcaggct gaaaatcttc tctcatccgc tcaatgatg atgatgatga    60 tggcg            65

<210> SEQ ID NO 17
<211> LENGTH: 51
<212> TYPE: DNA
<213> ORGANISM: Artificial sequence
<220> FEATURE:
<223> OTHER INFORMATION: Synthetic

<400> SEQUENCE: 17
ccatgaccct cgccggcggc ggcgccggcg gcatgggcac gttccagctg g            51

<210> SEQ ID NO 18
<211> LENGTH: 51
<212> TYPE: DNA
<213> ORGANISM: Artificial sequence
<220> FEATURE:
<223> OTHER INFORMATION: Synthetic

<400> SEQUENCE: 18
ccagctggaa cgtgcccatg ccgccggcgc cgccgccggc gagggtcatg g            51

<210> SEQ ID NO 19
<211> LENGTH: 51
<212> TYPE: DNA
<213> ORGANISM: Artificial sequence
<220> FEATURE:
<223> OTHER INFORMATION: Synthetic

<400> SEQUENCE: 19
ccatgaccct cgccggcggc ggcgccggcg gcatgggcac gttccagctg g            51

<210> SEQ ID NO 20
<211> LENGTH: 30

```
<212> TYPE: DNA
<213> ORGANISM: Artificial sequence
<220> FEATURE:
<223> OTHER INFORMATION: Synthetic

<400> SEQUENCE: 20
ctcctggccg gcatcgccct gaccttctcc                                        30

<210> SEQ ID NO 21
<211> LENGTH: 31
<212> TYPE: DNA
<213> ORGANISM: Artificial sequence
<220> FEATURE:
<223> OTHER INFORMATION: Synthetic

<400> SEQUENCE: 21
ccattcgtac caggtctggc cgaagccgtg c                                      31

<210> SEQ ID NO 22
<211> LENGTH: 25
<212> TYPE: DNA
<213> ORGANISM: Artificial sequence
<220> FEATURE:
<223> OTHER INFORMATION: Synthetic

<400> SEQUENCE: 22
ggtggcaagc agcacaaagt caccg                                             25

<210> SEQ ID NO 23
<211> LENGTH: 25
<212> TYPE: DNA
<213> ORGANISM: Artificial sequence
<220> FEATURE:
<223> OTHER INFORMATION: Synthetic

<400> SEQUENCE: 23
gcggaccttg tcgtgacggc cgtgg                                             25
```

MODULATORS OF THE ABC TRANSPORTER FAMILY AND METHODS FOR THEIR USE

This patent application is a divisional of U.S. application Ser. No. 11/691,595 filed Mar. 27, 2007, now abandoned which is a continuation-in-part of U.S. application Ser. No. 10/575,577, filed May 24, 2006, now abandoned which is the National Phase of PCT/US2004/033874 filed Oct. 14, 2004, which claims the benefit of priority from U.S. Provisional patent application Ser. No. 60/511,609, filed Oct. 15, 2003, the teachings of which are herein incorporated by reference in their entirety.

This invention was supported in part by funds from the U.S. government (NIH Grant No. P20-RR018787-01, NIH grant No. RO1 AI51360-01, NIH Grant No. RO1-DK45881, and NIH Grant No. RO1-DK34533). The U.S. government has certain rights in the invention.

FIELD OF THE INVENTION

A factor, confirmed using a proteomics approach to be a protein, which is secreted by Pseudomonas aeruginosa has now been identified as reducing plasma membrane expression of ATP-binding cassette (ABC) transmembrane proteins such as P-glycoprotein (Pgp or multidrug resistance protein (MDR)), multidrug resistance associated protein 2 (MRP2), Cystic Fibrosis Transmembrane Conductance Regulator (CFTR), and other members of the ABC transporter family, whose functions include control of the transport of small molecules across cell membranes. Inhibition of the expression of these ABC transmembrane proteins in the plasma membrane by this newly identified factor or active fragments or mimetics thereof is expected to be useful in promoting delivery of therapeutics to the central nervous system, treating cancers that have developed resistance to conventional therapies due to over expression of multidrug resistance transporters, increasing the bioavailability of drugs and in inhibiting secretory diarrhea. Suppression of the inhibitory effects of this newly identified factor on expression of ABC transmembrane proteins, particularly CFTR expression, is expected to be useful in treatment of patients with cystic fibrosis and other diseases of the respiratory tract that are caused by infection with Pseudomonas aeruginosa.

BACKGROUND OF THE INVENTION

A family of proteins found on the surface of cells is known as the ATP-binding cassette (ABC) family of transmembrane proteins. Expression of these proteins affects the therapeutic accumulation of drugs in the central nervous system as well as in cancer cells and affects the absorption of therapeutic drugs by the gastrointestinal tract. This family of proteins includes, but is not limited to, the transmembrane ATP-dependent drug translocation protein P-glycoprotein (Pgp; Nooter, K. and Sonneveld, P. *Leuk. Res.* 1993 18:233-243; Biedler, J. L. *Cancer Res.* 1994 54:666-678; Kerbel et al. *Cold Spring Harbor Symp. Quant. Biol.* 1994 59:661-672; Broxterman et al. *Curr. Opin. Oncol.* 1995 7:532-540; and List, A. F. *Leukemia* 1996 10:937-942), also referred to as the Multi-drug Resistance Protein (MDR), whose over expression is associated with multi-drug resistance (Demolombe, S, and Escande, D. *TIPS* 1996 17:273-275); and multidrug resistance associated protein 2 or MRP2, BCRP, MRP1, and the chloride channel Cystic Fibrosis Transmembrane Conductance Regulator (CFTR).

Pgp is expressed in a variety of normal tissues including liver, kidney and colon and in tumors arising from these tissues that usually over express Pgp as part of their multidrug resistance (MDR) phenotype (Cole et al. *Science* 1992 258:1650-1654; Roninson, I. B. *Biochem. Pharmacol.* 1992 43:95-102; Arceci, R. J. *Blood* 1993 81:2215-2222; and Merkel et al. *J. Clin. Oncol.* 1989 7:1129-1136). Pgp can also be over expressed in tumors from tissues that do not normally express this protein, such as breast and ovarian tissues (Arceci, R. J. *Blood* 1993 81:2215-2222; and Ihnat et al. *Clin. Cancer Res.* 1997 3:1339-1346). The mechanism of Pgp upregulation in tumors in vivo is still unclear, but can occur de novo as in acute myologenous leukemia (AML) (Gregorcyk et al. *Ann. Surg. Oncol.* 1996 3:8-14; Koh et al. *Yonsei Medical Journal* 1992 33:137-142; Dalton, W. S. and Sikic, B. I. *J. NIH Res.* 1994 6:54-58; Cole et al. *Science* 1992 258:1650-1654; Demolombe, S. and Escande, D. *TIPS* 1996 17:273-275; Schneider et al. *British J. Cancer* 1989 60:815-818; Fojo et al. *Proc. Natl. Acad. Sci. USA* 1987 84:265-269; Roninson, I. B. *Biochem. Pharmacol.* 1992 43:95-102; Arceci, R. J. *Blood* 1993 81:2215-2222; and Merkel et al. *J. Clin. Oncol.* 1989 7:1129-1136) or can be acquired over the course of cancer treatment as in breast and ovarian cancer (Merkel et al. *J. Clin. Oncol.* 1989 7:1129-1136; Ihnat et al. *Clin. Cancer Res.* 1997 3:1339-1346; Hamilton, J. W. and Wetterhahn, K. E. *Mol. Carcinogens* 1989 2:274-286; and McCaffrey et al. *Mol. Carcinogens* 1994 10:189-198).

MDR1 gene transcription and MDR1 mRNA expression can be induced by certain DNA damaging agents, including chemotherapeutic drugs such doxorubicin, alkylating agents such as methyl methanesulfonate, and genotoxic chemical carcinogens that induce bulky DNA adducts such as aflatoxin B1 and 2-acetylaminofluorene.

MRP1, MRP2, and BCRP are also members of the ABC family of transmembrane proteins involved in the transport of small therapeutic drugs and other molecules across cell membranes.

CFTR, another member of the ABC family of transport proteins is a cAMP-regulated chloride channel that mediates transepithelial chloride transport in the airways, intestine, pancreas, testis and other tissues. Cystic fibrosis, a lethal genetic disease, is caused by mutations in the CFTR gene, the most common of which is ΔF508. Intestinal CFTR contributes to the massive fluid and electrolyte losses in secretory diarrhea (Al-Awqati, Q. J. Clin. Invest. 2002 110(11):1599-601; Kunzelman et al. Physiol. Rev. 2002 82(1):245-89).

The ability to modulate the expression of these proteins has broad applications in a variety of clinical situations including, but not limited to, prevention of multidrug resistance in cancer, delivery of therapeutics to the central nervous system, inhibition of secretory diarrhea, and treatment of cystic fibrosis.

SUMMARY OF THE INVENTION

An object of the present invention is to provide a composition comprising an isolated factor confirmed, using a proteomics approach to be a protein, or an active fragment thereof, derived from the bacterium Pseudomonas aeruginosa that reduces expression of ABC transmembrane proteins in the plasma membrane.

Another object of the present invention is to provide a composition comprising a mimetic of the isolated factor, or an active fragment thereof, derived from the bacterium Pseudomonas aeruginosa that reduces expression of ABC transmembrane proteins in the plasma membrane for use in combination therapies for CNS disorders, infections and diseases and cancers exhibiting multidrug resistance.

Another object of the present invention is to provide a method for modulating plasma membrane expression of an ABC transmembrane protein in a cell comprising administering to the cell of the isolated factor, or active fragment thereof, derived from *Pseudomonas aeruginosa* or a mimetic thereof that modulates plasma membrane expression of ABC transmembrane proteins.

Another object of the present invention is to provide a method for delivering a small molecule therapeutic agent to the central nervous system of a subject which comprises administering to the subject the isolated factor or active fragment thereof derived from *Pseudomonas aeruginosa* or a mimetic thereof that reduces expression of ABC transmembrane proteins in the plasma membrane so that expression of ABC transmembrane proteins which prevent small molecules from accumulating in the central nervous system is inhibited in the subject and administering to the subject the small molecule therapeutic agent.

Another object of the present invention is to provide a method for treating cancer in a subject which comprises administering to the subject the isolated factor or active fragment thereof derived from *Pseudomonas aeruginosa* or a mimetic thereof that reduces plasma membrane expression of ABC transmembrane proteins so that expression of ABC transmembrane proteins which confer drug resistance in cancer cells is inhibited in the subject and administering to the subject an anti-cancer agent. This method of treating cancer is particularly useful in cancers that have become resistant to therapy due to overexpression of ABC transmembrane proteins and/or to cancers of the central nervous system.

Another object of the present invention is to provide a method for treating secretory diarrhea in a subject which comprises administering to the subject the isolated factor or active fragment thereof derived from *Pseudomonas aeruginosa* or a mimetic thereof that reduces plasma membrane expression of ABC transmembrane proteins, and in particular intestinal CFTR expression, so that massive fluid and electrolyte losses in secretory diarrhea are inhibited.

Another object of the present invention is to provide agents and methods for identifying agents which inhibit or suppress this *Pseudomonas aeruginosa* and active fragments thereof and their inhibitory effects on expression of ABC transmembrane proteins, particularly CFTR expression.

Another object of the present invention is to provide a method for increasing the bioavailability of drugs by reducing the membrane expression of ABC transporters in the intestine, kidney and liver.

Yet another object of the present invention is to provide compositions and methods for treating or alleviating symptoms of a subject suffering from cystic fibrosis via administration of a composition comprising an agent which inhibits or suppresses this *Pseudomonas aeruginosa* factor and its inhibitory effects on expression of ABC transmembrane proteins, particularly CFTR expression.

DETAILED DESCRIPTION OF THE INVENTION

A factor, confirmed using a proteomics approach to be a protein, which is secreted by clinical isolates of the bacterium *Pseudomonas aeruginosa* has now been identified that reduces or otherwise modulates the plasma membrane expression of CFTR as well as P-glycoprotein (i.e. Pgp or multidrug resistance protein (MDR)), MRP2, MRP1, BCRP and other members of the ABC transmembrane protein family, whose functions include the transport of small molecules, including but not limited to ions, across cell membranes. More specifically, members of the ABC transporter family function by preventing therapeutics including but not limited to anti-cancer therapeutics and antibiotics from accumulating in the central nervous system, and by conferring the observed "drug resistance" of numerous cancers.

The factor of the present invention that reduces or otherwise modulates the plasma membrane expression of the ABC transmembrane protein family is secreted by *P. aeruginosa* during the stationary phase. This factor has been found to be heat-labile and its activity is extended in the presence of protease inhibitors. The factor is retained by a membrane with a reported molecular weight cut-off of greater than 30 kDa. The factor of the present invention remains in solution in the presence of 70% ammonium sulfate and it interacts with the anion exchange resin at pH 6.5. Thus, the factor was believed to be a protein. The factor was partially purified with ion exchange chromatography, ammonium sulfate precipitation, and gel filtration.

Studies were conducted demonstrating that *P. aeruginosa* affects the apical membrane expression of ABC transporters including CFTR, Pgp, BCRP and MRP2 in polarized epithelial cells. In these experiments two human cell lines endogenously expressing CFTR, Pgp, BCRP and MRP2, and polarized canine and rat cells stably expressing wild-type (wt)-CFTR and/or Pgp, were contacted with a pelleted fraction of either *P. aeruginosa* strain PA14 or eight different clinical isolates. Apical membrane expression of CFTR, Pgp, and MRP2 was measured by cell-surface biotinylation. Epithelial cells were then lysed and biotinylated proteins were isolated, separated and amounts of apical membrane expression of CFTR, PgP and MRP2 were determined.

PA14 reduced by >80% the apical membrane expression of endogenous CFTR in human cells and canine cells expressing wt-CFTR compared to heat-killed PA14 or vehicle alone as well. PA14 also decreased by >80% the apical membrane expression of wt-CFTR in rat cells. The effect of PA14 was not general for all plasma membrane proteins because PA14 had no effect on the apical membrane expression of glycoprotein gp114 or on the basolateral membrane expression of Na-K-ATPase or the transferrin receptor. All eight clinical isolates of *P. aeruginosa* tested also decreased the apical plasma membrane expression of wt-CFTR in canine cells.

To determine whether PA14 reduces apical membrane expression of CFTR via direct or indirect interactions with epithelial cells, apical membranes in the human, canine and rat cells were incubated with the cell-free PA14 filtrate containing factors secreted by PA14. The PA14 filtrate decreased the apical membrane expression of CFTR by >80% in all cell lines tested in 15 minutes compared to heat-inactivated PA14 filtrate or vehicle alone.

PA14 ($5 \times 10^7$ CFU/ml) and the cell-free PA14 filtrate containing the PA14 secreted factors decreased by >70% the apical membrane expression of endogenous Pgp in both human cell lines. Similar results were observed in canine cells stably expressing Pgp. PA14 filtrate decreased by >70% the apical membrane expression of endogenous MRP2 in human cells compared to vehicle control as well.

Taken together, these observations support the conclusion that a heat-labile factor secreted by *P. aeruginosa* reduces the apical membrane expression of ABC transporters including CFTR, Pgp, BCRP and MRP-2 in polarized epithelial cells.

The ability of this secreted factor to inhibit expression of these transporters in the plasma membrane is indicative of its utility in facilitating delivery of small molecule therapeutic agents to the central nervous system, for enhancing efficacy of antibiotics as well as anti-cancer agents, particularly in multidrug resistant cancers and cancers of the central nervous system, and inhibiting massive fluid and electrolyte losses in secretory diarrhea. Moreover, this secreted factor will enhance the bioavailability of drugs by facilitating their absorption by the gastrointestinal tract.

The above experiments were performed using partially purified factor or isolated factor from clinical isolates of the bacterium *Pseudomonas aeruginosa*. However, as will be understood by those of skill in the art upon reading this disclosure, the factor and fragments thereof can be isolated, or prepared recombinantly or synthetically. Accordingly for purposes of the present invention, by the phrase "an isolated factor or protein derived from the bacterium *Pseudomonas aeruginosa*" it is meant to encompass the secreted factor, purified or partially purified from the bacterium as well as proteins having the same amino acid sequence as this factor but which are prepared recombinantly or synthetically using well known techniques.

Further, fragments of this factor may exhibit similar inhibitory activities. Such fragments are referred to herein as active fragment or active peptide fragments. By "active fragment" or "active peptide fragment" it is meant a peptide shorter in amino acid sequence than the full-length factor but which exhibits the same or similar activity as an inhibitor of transmembrane receptor protein expression. Active fragments can be isolated from the bacterium or prepared recombinantly or synthetically in similar fashion to the full-length factor.

The identification of this factor, confirmed to be a protein, and its function as an inhibitor of transmembrane protein expression also enables the development of mimetics of this factor or active fragments thereof with similar ability to reduce expression of ABC transmembrane proteins in cells. By "mimetic", as used herein it is meant to encompass peptidomimetics as well as small organic molecules similar in structure and/or inhibitory function to the factor or active fragments of the factor isolated from *Pseudomonas aeruginosa*.

Factors and active fragments thereof derived from the bacterium *Pseudomonas aeruginosa* that reduce expression of ABC transmembrane proteins or mimetics thereof can be administered in compositions further comprising a physiological acceptable vehicle to cells to inhibit the expression of an ABC transmembrane protein in the cells.

Inhibiting expression of an ABC transmembrane protein is expected to be useful in facilitating delivery of small molecule therapeutic agents to the central nervous system of a subject. In this method, the composition comprising the isolated factor or protein or active fragment thereof or mimetic thereof is administered to the subject so that plasma membrane expression of an ABC transmembrane protein which prevents small molecules from entering the central nervous system is inhibited. The small molecule therapeutic agent to be delivered to the central nervous system is also administered, preferably systemically, simultaneously or after the composition, to the subject without inhibition of accumulation of the therapeutic agent in the central nervous system by ABC transporter proteins. Examples of small molecule therapeutic agents which can be delivered to the central nervous system by this method include, but are not limited to, antibiotics and anti-cancer agents.

Inhibiting plasma membrane expression of an ABC transmembrane protein is also expected to be useful in enhancing efficacy of cancer treatments or other therapeutics, particularly in cancer of the central nervous system and multidrug resistant cancers. In this method, a subject is administered the composition comprising the isolated factor or protein or active fragment thereof or a mimetic thereof so that expression of an ABC transmembrane protein which prevents small molecules from accumulating in the CNS or which confers drug resistance in cancer cells is inhibited in the subject. The anti-cancer agent is administered to the subject, before, simultaneously or after the subject is exposed to the composition.

The factor of the present invention secreted by *P. aeruginosa* works quickly within approximately 5 to 10 minutes. Accordingly, it is believed that a therapeutic agent can be delivered simultaneously or within 5 to 10 minutes of administration of the compositions comprising the factor or protein or active fragment thereof or the mimetic thereof.

The demonstrated ability of this factor to decrease transmembrane CFTR expression is also indicative of its utility in treating secretory diarrhea in a subject. In particular, it is expected that administration of a composition comprising the isolated factor or protein or active fragment thereof derived from *P. aeruginosa* or a mimetic thereof which reduces expression of ABC transmembrane proteins, and in particular intestinal CFTR expression, will inhibit the massive fluid and electrolyte losses from CFTR in secretory diarrhea.

Further, compositions comprising the isolated factor or protein or active fragment thereof derived from *P. aeruginosa* or a mimetic thereof are expected to be useful in increasing efficacy of anti-cancer and other therapeutics by increasing their bioavailability upon oral administration. In this embodiment, a composition of the present invention is administered orally with the anticancer drug or other therapeutic, thereby increasing gastrointestinal absorption and reducing secretion into bile of the anticancer drug or other therapeutic agent and resulting in an increase in its bioavailability. In this embodiment, the anti-cancer agent or other therapeutic is administered orally to the subject, before, simultaneously or after the subject is orally administered the composition.

Formulations of a therapeutic agent with increased oral bioavailability can also be prepared comprising the therapeutic agent and a composition comprising the isolated factor or protein or active fragment thereof derived from *P. aeruginosa* or a mimetic thereof.

By "subject" as used herein, it is meant to be inclusive of any mammal, including but not limited to humans.

In this embodiment, the factor or protein, active fragment thereof, or mimetic thereof is preferably administered intravenously in a formulation acceptable for intravenous administration or orally in a formulation acceptable for oral administration and in an amount sufficient to inhibit expression of ABC transmembrane proteins. However, as will be understood by those of skill in the art, alternative modes of administration and formulations acceptable for these alternative modes of administrations are within the scope of this invention.

Further, this heat-sensitive factor secreted by *P. aeruginosa* has been found to reduce CFTR-mediated, transepithelial Cl− secretion across polarized human airway epithelial cells in cells expressing ΔF508-CFTR, the most common mutation in cystic fibrosis.

These experiments were conducted in CFBE41o− cells stably expressing either wt-CFTR or ΔF508-CFTR and in parental (non-transfected ΔF508/ΔF508) CFBE41o− cells. To increase apical membrane expression of ΔF508-CFTR, cells were grown at 27° C. for 36 hours in accordance with methods set forth in Example 5. To control for any possible effects of reduced temperature on the results, parental and wt-CFTR expressing cells were also grown at 27° C. for 36 hours. As determined by cell surface biotinylation, reduced temperature had no effect on the apical membrane expression of wt-CFTR but significantly increased plasma membrane expression of ΔF508-CFTR. Parental CFBE41o− cells, and CFBE41o− cells stably expressing either wt-CFTR or ΔF508-CFTR were incubated at 27° C. in a $CO_2$ incubator in the absence of antibiotics. Vehicle or PA14 bacteria ($5\times10^8$ CFU/ml) were added to the apical side of the monolayers. PA14 inhibited the glybenclamide-sensitive, forskolin and genistein stimulated Isc in CFBE41o– stably expressing wt- and ΔF508-CFTR after 4-6 hours of incubation. The effect was not observed after exposing the apical side of the monolayers to PA14 for <3 hours. The parental CFBE41o– cells had no detectable glybenclamide-sensitive Isc before or after stimulation with genistein or forskolin, and PA14 had no effect on the Isc either before or after addition of genistein or forskolin. Taken together these observations confirm that P. aeruginosa inhibits CFTR-mediated Cl– secretion in polarized human airway epithelial cells expressing wt-CFTR, and extend these observations to reveal that PA14 also inhibits ΔF508-CFTR-mediated Cl– secretion in polarized, human airway epithelial cells.

Experiments were then performed to determine whether the inhibition of Isc was reversible. In these experiments CFBE41o– cells stably expressing either wt-CFTR or ΔF508-CFTR were first incubated with vehicle or PA14 bacteria as described supra. After 6 hours of incubation, the monolayers were washed and subsequently incubated at 37° C. in a $CO_2$ incubator with sterile media containing antibiotics. One hour after washing off the bacteria from the apical side of CFBE41o– monolayers the glybenclamide-sensitive, forskolin and genistein stimulated Isc recovered to control values. These observations indicate that P. aeruginosa reversibly inhibits CFTR-mediated Cl– secretion in intact, polarized human airway epithelial cells.

The effects of P. aeruginosa on CFTR mediated Cl– secretion across polarized MDCK (kidney) cells stably expressing wt- or ΔF508-CFTR were examined as well. It was found that addition of PA14 (4-6 hour incubation at 37° C. with $5\times10^6$ CFU/ml washed PA14 bacteria added to the apical solution) inhibited CPT-cAMP stimulated Isc in the wt- and ΔF508-CFTR expressing cells. Taken together these observations demonstrate that P. aeruginosa inhibited CFTR-mediated Cl– secretion in polarized human airway epithelial cells and polarized kidney epithelial cells stably expressing wt- or ΔF508-CFTR.

Experiments were then performed demonstrating that PA14 reversibly inhibits Isc across polarized human airway epithelial cells at least in part by decreasing the number of CFTR channels in the apical plasma membrane.

To determine whether P. aeruginosa decreased the expression of CFTR in the apical plasma membrane, polarized MDCK cells were incubated with vehicle or PA14 bacteria ($5\times10^6$ CFU/ml added to the apical medium in the absence of antibiotics) and the apical membrane expression of CFTR was measured by cell surface biotinylation. PA14 decreased the apical membrane expression of CFTR after 4-6 hours of incubation compared to vehicle or heat-killed PA14. The effect was not observed after exposing the apical side of the monolayers to PA14 for $\leq3$ hours. PA14 did not affect the expression of gp114 in the apical plasma membrane or the expression of either the Na,K-ATPase or the transferrin receptor expressed in the basolateral plasma membrane. Expression of ΔF508-CFTR in the apical membrane of MDCK cells was too low to examine by cell surface biotinylation, thus, the effect of PA14 on the apical membrane expression of ΔF508-CFTR could not be measured. PA14 also decreased the expression of CFTR in the apical plasma membrane of Calu-3 cells and inhibited the expression of wt-CFTR and ΔF508-CFTR in the apical plasma membrane of CFBE41o– cells.

To determine whether this decrease in the expression of CFTR in the apical membrane was reversible, CFBE41o– cells stably expressing either wt-CFTR or ΔF508-CFTR were first incubated with vehicle or PA14 bacteria as described supra. After 6 hours of incubation, the monolayers were washed and subsequently incubated at 37° C. in a $CO_2$ incubator with sterile media containing antibiotics. One hour after washing off the bacteria from the apical side of CFBE41o– monolayers, CFTR expression in the apical membrane recovered to control values. These observations indicate that P. aeruginosa reversibly inhibits the apical membrane expression of CFTR in intact polarized human airway epithelial cells.

Additional experiments were performed demonstrating that clinical isolates of P. aeruginosa affect the plasma membrane expression of CFTR. The effects of 12 clinical isolates of P. aeruginosa, 6 cultured from CF patients and another 6 obtained from non-CF patients were examined. To determine whether the clinical isolates of P. aeruginosa decreased the expression of CFTR in the apical plasma membrane, polarized MDCK cells were incubated with vehicle or $5\times10^6$ CFU/ml washed clinical isolates of P. aeruginosa, added to the apical solution, and the apical membrane expression of CFTR was measured by cell surface biotinylation. The clinical isolates also decreased the expression of CFTR in the apical membrane (percent decrease: $31\pm6.5\%$; n=3/each clinical isolate, $p<0.05$).

Experiments were then performed demonstrating that inhibition of CFTR expression in the apical membrane is mediated by the heat-sensitive factor secreted by P. aeruginosa described herein. In these experiments bacteria-free PA14 filtrate was prepared as described in Example 2. Vehicle or PA14 filtrate was added to the apical side of polarized MDCK monolayers, and the apical membrane expression of CFTR was measured by cell surface biotinylation. The PA14 filtrate rapidly (in minutes) decreased expression of CFTR in Calu-3 cells and inhibited the expression of wt-CFTR and ΔF508-CFTR in the apical membrane in CFBE41o– cells. Heating the PA14 filtrate resulted in loss of this activity.

This heat-sensitive factor secreted by P. aeruginosa was then demonstrated to inhibit recycling of CFTR from endosomes to the apical membrane. In these experiments, the endocytic recycling of CFTR was measured at 1, 3, and 5 minutes as described in Example 7. It was found that P. aeruginosa reduces the apical membrane expression of CFTR by rapidly inhibiting the recycling of CFTR from an endosomal pool back to the apical plasma membrane.

Data from these experiments provide direct evidence that P. aeruginosa inhibits the endocytic trafficking of CFTR in intact polarized human airway epithelial cells.

Cystic fibrosis patients are born with histologically normal lungs that become colonized with inhaled bacteria soon after birth, due to failure of the innate immunity of the airway. The early bacterial airway infection is accompanied by an intense neutrophilic inflammatory response in the peribronchial and endobronchial spaces. Subsequently, after several months to years, progressive obstructive pulmonary disease associated with chronic P. aeruginosa infection develops in approximately 80% of cystic fibrosis patients and, eventually, leads to respiratory failure and death. The density of P. aeruginosa in the airway increases with age of the cystic fibrosis patients. Colony counts of P. aeruginosa obtained in cystic fibrosis patients during bronchoscopy after lavaging the bronchus with 10-60 ml of sterile normal saline range from $10^2$ to >$10^5$ CFU/ml of the bronchalveolar lavage fluid. In direct quantitative sputum cultures from cystic fibrosis patients the colony counts are higher and range from $10^7$ to $10^9$ CFU/ml or gram of sputum. In cystic fibrosis patients the decline in pulmonary function correlates with the density of *P. aeruginosa* in the lower airway and is worse with $\geq 10^5$ CFU/ml bronchalveolar lavage fluid. In addition, in severely-ill non-cystic fibrosis patients with pneumonia, colony counts $\geq 10^4$ CFU/ml bronchalveolar lavage fluid may be present despite antibiotic treatment.

Because *P. aeruginosa* decreases CFTR-mediated Cl- transport in polarized human airway epithelial cells at concentrations ($5 \times 10^6$-$5 \times 10^8$ CFU/ml) comparable to those described above in human airway, experiments described herein indicate that similar inhibition of Cl- transport may occur in the airway during infection with *P. aeruginosa*. Thus, it is believed that restoration of CFTR-mediated Cl- transport and mucociliary clearance by a combined therapy including: (1) promoting ΔF508-CFTR exit from the endoplasmic reticulum, (2) activating ΔF508-CFTR in the apical plasma membrane, and (3) increasing the half-life of ΔF508-CFTR in the apical membrane may be compromised by the presence of chronic and irreversible infection with *P. aeruginosa*. Based upon experiments described herein, however, it is expected that Cl- transport can be restored and the innate immunity in the airway reinstated in these patients by including in this therapy an additional agent which inhibits or suppresses the isolated *Pseudomonas aeruginosa* factor of the present invention and its inhibitory effects on expression of ABC transmembrane proteins, particularly CFTR expression.

A proteomics approach was used to confirm that this factor is secreted protein PA2934 (Genbank Accession No. AE004091; Stover et al. Nature 2000 406:959-964; SEQ ID NO:1). The gene for this protein was identified and is referred to herein as cif, for CFTR inhibitory factor (depicted in SEQ ID NO:2).

Demonstrated herein is that Cif is a secreted protein and is found associated with membrane-derived vesicles. Further, expression of Cif in *E. coli* and purification of the C-terminal 5xHis-tagged Cif protein showed that Cif is necessary and sufficient to mediate the reduction in apical membrane expression of CFTR and a concomitant reduction in CFTR-mediated Cl- ion secretion. Cif demonstrates epoxide hydrolase activity in vitro, and requires a highly conserved histidine residue conserved in α/β hydrolase family enzymes to catalyze this reaction. Mutating this histidine residue abolishes the ability of Cif to reduce apical membrane CFTR expression. Further, it has been confirmed that the cif gene is expressed in the Cystic Fibrosis lung and non-mucoid isolates of *P. aeruginosa* show greater expression of the gene than mucoid isolates. Thus, it is believed that the Cif-mediated decrease in apical membrane expression of CFTR by environmental isolates of *P. aeruginosa* facilitates the colonization of the Cystic Fibrosis lung by this microbe.

To determine the identity of CIF, cell-free supernatant was fractionated from stationary phase cultures utilizing anion exchange chromatography and a step gradient of NaCl, and the resulting fractions were assayed for their ability to decrease apical expression of CFTR in WT-CFBE cells. Crude supernatant of *P. aeruginosa* PA14 reduced apical membrane CFTR expression to ~20% of the WT level. Upon fractionation of the supernatant, it was found that the two flow-through fractions (F1, F2) and the fraction resulting from washing the column with 0 mM NaCl (wash) lacked CIF activity. However, the CIF activity was eluted from the column with 50 mM NaCl. Fraction E1 resulted in <5% of WT apical membrane CFTR expression. E2, a subsequent second fraction eluted with 2 M NaCl, also showed some CIF activity.

SDS-PAGE analysis of the fractions demonstrated that while fraction E1 is less complex than the crude supernatant, it still contained approximately 25 proteins.

The proteins in the CIF-containing fractions were identified utilizing multidimensional protein identification technology (MudPIT). Peptide masses from the MudPIT analysis were compared to the *P. aeruginosa* PA14 protein database (NCBI nr 40070473) resulting in the identification of 20 proteins from the E1 fraction.

Based upon secretion of the isolated factor and size exclusion chromatography demonstrating the secreted factor to be greater than 30 kDa in mass, candidate proteins were prioritized based on size, presence of secretory signals predicted by SMART (smart with the extension .embl-heidelberg.de/ of the world wide web) and predicted localization (PSORT, psort with the extension .nibb.ac.jp/ of the world wide web). The top three candidate proteins, PA1914, PA2934 and PA4476, were selected for further study.

Single crossover mutations were created in the PA1914, PA2934 and PA4476 genes and the resulting mutants were assayed for their ability to decrease apical expression of CFTR. Disrupting either the PA1914 or the PA4476 genes did not result in any loss of CIF activity. Mutating the PA2934 gene with a single crossover knockout mutation resulted in a complete loss of CIF activity, as does deletion of the PA2934 gene.

The PA2934 gene was cloned into the multi-copy, arabinose inducible plasmid pMQ70 alone or with a penta-histidine tag fused onto the carboxy-terminus of the protein resulting in the plasmids pDPM70 and pDPM73, respectively. Expression of the WT PA2934 protein from a multi-copy plasmid or a His-tagged variant of PA2934 (pDPM73/PA2934-His) was capable of complementing the mutation, thus demonstrating that a functional PA2934 protein is necessary for the CIF activity. Furthermore, these data indicate that adding a His-Tag to the C-terminus of PA2934 has no apparent impact on the function of the protein.

Experiments were then performed to determine if *E. coli*, which had previously been shown to lack CIF activity, demonstrated CIF activity when the PA2934-His protein was expressed in trans from a plasmid. Indeed, although *E. coli* had no CIF activity, when the PA2934-His protein was expressed in *E. coli* from an arabinose inducible promoter on a multi-copy plasmid, the resulting culture supernatants were capable of reducing apical membrane expression of CFTR.

Western blot analysis was performed of whole cell and supernatant fractions of *P. aeruginosa* carrying a plasmid which expressed PA2934-His (pDPM73), or the vector only control (pMQ70) to confirm that PA2934 was a secreted protein. A cross-reacting band was detected in both the whole cell (WC) and supernatant (S) fraction of the PA2934-His expressing strain, but not the strain carrying the vector, when probed with anti-His-tag antibody. To confirm that the supernatant localized PA2934-His was not a result of cell lysis, it was demonstrated that SadB, a known cytoplasmically localized protein, was detected in the whole cell, but not the supernatant fraction of these same WT/pPA2934-His-derived samples. These data indicate that the PA2934-His protein found in the supernatant was not due to cell lysis. Taken together with the predicted Sec-secretion signal sequence at the N-terminus of PA2934 and the activity assays described herein, these data indicate that PA2934 is indeed the secreted factor.

Several recent reports have shown that *P. aeruginosa* and other microbes package extracellular signaling molecules and toxins in outer membrane derived vesicles (OMV) (Demuth et al. Cell Microbiol 2003 5:111-121; Kesty et al. Embo J 2004 23:4538-4549; Mashburn, L. M. and Whiteley, M. Nature 2005 437:422-425). Furthermore, enterotoxigenic *E. coli* has been shown to deliver a toxin to a eukaryotic host via its OMVs (Kesty et al. Embo J 2004 23:4538-4549). Given that PA2934 is a secreted protein and impacts eukaryotic cell function, association of PA2934 with extracellular vesicles was examined.

In studies using PA2934-His expressed from a plasmid, it was determined that PA2934-His was found both in the soluble fraction and the pellet after centrifugation of cell supernatants at 40,000 g, conditions which are known to pellet membrane vesicles (Horstman, A. L. and Kuehn, M. J. J Biol Chem 2000 275:12489-12496).

Association of WT PA2934 protein expressed from its native context with vesicles was then examined. Membrane vesicles were prepared from the WT and the ΔPA2934 mutant and the vesicle-containing fractions were probed with polyclonal antibody to the PA2934 protein. Consistent with the localization of PA2934 protein to vesicles, a cross-reacting band migrating at the expected molecular weight of approximately 33 kDa was observed in the vesicle fraction of the WT but not the ΔPA2934 mutant strain. Furthermore, these same fractions were probed with a polyclonal antibody to the outer membrane protein OprF, because vesicles have been shown to accumulate outer membrane proteins (Schooling, S. R. and Beveridge, T. J. J Bacteriol 2006 188:5945-5957). A cross-reacting band of the expected size was detected in the vesicle fraction of the WT but not the oprF mutant. These data indicate that PA2934 is likely associated with membrane vesicles.

To demonstrate that PA2934 was both necessary and sufficient for CIF activity, the PA2934-His protein was purified from culture supernatants. The His-tag variant was exploited thereby allowing purification of PA2934-His on a nickel chelate affinity column. The PA2934-His protein could be detected in crude cell-free lysates of an arabinose-induced *E. coli* strain expressing this protein from an arabinose inducible promoter (pDPM73). Using the His-affinity resin, the PA2934-His protein was purified to apparent homogeneity from culture supernatants.

When the purified PA2934-His was applied to WT-MDCK cells, it was capable of a time dependent reduction of apical membrane expression of CFTR. By 60 minutes after treatment with PA2934-His, the apical expression of CFTR was reduced by >60%, and by >70% at 90 minutes. Similar results were obtained when PA2934-His was applied to the apical surface of WT-CFBE cells, indicating that the effects of PA2934-His on CFTR are not cell-line dependent. These data demonstrate that PA2934 is both necessary and sufficient for the CIF activity thus resulting in our referring to the PA2934 gene and the resulting protein product cif and Cif, respectively, for CFTR inhibitory factor.

As shown herein supra, the decrease in apical expression of CFTR following treatment with CIF-containing culture supernatants was accompanied by a decrease in CFTR mediated chloride secretion. In order to demonstrate that the purified Cif is sufficient for both the decreased apical expression of CFTR, as well as the decrease in CFTR mediated chloride secretion, Ussing chamber experiments were repeated using the purified Cif-His protein. Purified Cif-His protein added to the apical face of these cells inhibited the forskolin stimulated CFTR-mediated Cl$^-$ ion secretion by almost 30 μA/cm$^2$, whereas buffer alone had no significant effect on forskolin stimulated CFTR Cl current. As a control, addition of the specific CFTR inhibitor CFTR$_{inh}$-172 to WT-CFBE cells reduced forskolin stimulated, CFTR-mediated Cl$^-$ ion secretion by almost 50 μA/cm$^2$. Thus, recombinant CIF-His reduced CFTR Cl$^-$ currents by approximately 60% and apical plasma CFTR Cl$^-$ ion channel expression by approximately the same amount.

The ability of Cif to decrease apical CFTR expression and reduce the CFTR-mediated Cl$^-$ ion secretion is indicative of Cif activity having a functional impact on the biology of airway cells relevant to CF. Further, the demonstration herein that Cif is a secreted protein and that supernatants of *P. aeruginosa* are sufficient to observe Cif activity indicates that direct contact of the bacteria with the airway cells is not necessary for Cif to exert its affects on these cells. In addition, data showing Cif to be associated with membrane vesicles indicates that fusion of the diffusible vesicles with the epithelial cells may be one mechanism by which Cif enters the cytosol of eukaryotic cells. It has been suggested that biofilms of *P. aeruginosa* in the CF lung may form in the mucus above the airway cells rather than directly on the airway cells (Worlitzsch et al. J. Clin. Invest. 2002 109:317-325). However, given that Cif is secreted and likely diffusible in the context of the CF lung and that purified Cif protein in the absence of bacteria is sufficient to decrease apical membrane CFTR expression, it is believed that this toxin is capable of impacting airway cell biology in CF even if expressed from bacteria in the mucus.

While the alteration of trafficking is relatively commonplace amongst intracellular pathogens, it is not typically associated with extracellular pathogens such as *P. aeruginosa*. Therefore, Cif-mediated alteration of CFTR trafficking may represent a novel mechanism of altering the cell biology of the host by an extracellular pathogen. It is believed that the alteration of protein localization following secretion of Cif may create an environment conducive for *P. aeruginosa* colonization. That is, in the context of CF, Cif may further reduce any residual Cl$^-$ ion secretion and airway surface liquid volume, and thereby further reduce mucociliary clearance, allowing establishment of the *P. aeruginosa* infection and eventually biofilm formation.

The Cif protein is predicted to belong to a large family of proteins known as the α/β hydrolases. This superfamily is comprised of several sub-families of proteins including acyltransferases, lipases, lysophospholipases and epoxide hydrolases. Further examination of the protein sequence suggested that Cif contains domains consistent with an epoxide hydrolase, a diverse family of proteins associated with degradation of xenobiotic compounds and involved in mammalian cell signaling.

To assess whether Cif acts as an epoxide hydrolase, its ability to degrade the synthetic epoxide hydrolase substrate (2S,3S)-trans-3-Phenyl-2-oxiranylmethyl 4-nitrophenyl carbonate ((S)-NEPC) was assessed. This assay measures the production of the product p-nitrophenol, which is yellow in color and absorbs maximally at 405 nm. It was found that purified Cif is capable of degrading this compound in a protein concentration dependent manner during the 60 minute incubation period of this assay.

Members of the α/β hydrolase family, including typical epoxide hydrolases, are characterized by the presence of a catalytic triad consisting of a nucleophile, acidic residue, and an invariant histidine located within three separate loops of the protein (Holmquist, M. Curr Protein Pept Sci 2000 1:209-235). Examination of the amino acid sequence of Cif identified these residues including the invariant Histidine residue. A mutant variant of Cif was created in the purification vector, wherein the histidine residue at position 269 was replaced with an alanine residue. Western blot analysis of *E. coli* expressing either Cif-His or the Cif-His(H269A) variant demonstrated that the H269A variant was stably expressed.

The Cif-His(H269A) protein was purified to apparent homogeneity using the same method described for the WT Cif-His protein, and assayed for epoxide hydrolase activity as described above. The H269A mutation significantly reduced the epoxide hydrolase activity of this variant as compared to the WT protein, resulting in activity at or near levels seen for the buffer control.

To correlate epoxide hydrolase activity with CIF activity, the ability of the purified H269A variant of Cif to decrease apical expression of CFTR was tested. It was found that while the WT Cif-His protein significantly decreases the apical expression of CFTR, the Cif-H269A mutant protein had no effect on the apical expression of CFTR in WT-MDCK cells. Similarly, the Cif(H269A)-His mutant protein had little or no effect on CFTR mediated Cl⁻ secretion in WT-CFBE cells. These data, along with the demonstration that the H269A mutant lacks epoxide hydrolase activity, suggests that the epoxide hydrolase activity is linked to Cif activity.

To better understand the clinical relevance of Cif activity, cif expression was characterized in *P. aeruginosa* clinical isolates and specifically those isolates that originated from Cystic Fibrosis patients. To do this, the clinical isolates from CF patients were divided into either mucoid or non-mucoid strains based on their phenotypes on solid LB medium. Non-mucoid strains are typically associated with early infection of the CF lung, while mucoid strains are associated with chronic lung infections (Deretic et al. Biotechnology (N Y) 1993 11:1133-1136; Deretic et al. Trends Microbiol 1995 3:351-356; and Martin et al. Proc Natl Acad Sci USA 1993 90:8377-8381).

To quantitatively assess cif gene expression, strains were grown in LB medium to an $OD_{600}$ of approximately 2.5, the total cellular RNA harvested and quantitative real time PCR (qRT-PCR) was performed. Expression of the cif gene was significantly higher in all 5 non-mucoid clinical isolates as compared to strain *P. aeruginosa* PA14 and the mucoid *P. aeruginosa* strains.

To investigate the role of cif in the context of the CF lung, expression of this gene in the population of *P. aeruginosa* residing in sputum within the CF lung was examined. Total RNA was purified from the sputum of two CF patients, cDNA synthesized and the expression of the cif gene assessed by qRT-PCR reactions. The cif gene transcript was detectable in the sputum sample in both patients tested, as is the constitutively expressed rplU gene, suggesting that cif is transcribed in the CF airway.

The demonstration that cif transcript is detectable within CF sputum is indicative of the protein product of this gene being expressed within the CF airway and contributing to the pathogenesis of *P. aeruginosa* in this context. Furthermore, the data demonstrating that cif gene expression is relatively high in non-mucoid isolates, which are associated with early colonization of the CF lung, and relatively low in mucoid isolates, which are associated with the long term chronic colonization of the CF lung, suggests that cif expression may be temporal in nature. That is, cif gene expression may be important early in the colonization of the CF lung, but play little or no role in the later chronic infection processes.

Thus, from these experiments, it is believed that CF lung infection may occur in two stages, wherein Cif plays a key role in the first stage of infection, perhaps by further reducing CFTR expression in CF patients and thus facilitating subsequent biofilm formation by this microbe. In this two-stage model of CF lung infection, *P. aeruginosa* enters the lung and may be able to gain an initial foothold due to the decreased expression of CFTR in a CF patient and the associated decrease in mucocilliary clearance and other innate resistance pathways. *P. aeruginosa* strains expressing Cif may have a selective advantage in continued persistence in the lung because these organisms can further decrease the already depleted levels of apical membrane CFTR, thus resulting in the inability of the lung to clear this microbe. As lung function decreases the bacterial infection progresses leading eventually to biofilm formation and the mucoid phenotype, wherein Cif function is no longer required and therefore there may be a selective advantage in down regulating its expression. This model could account for why *P. aeruginosa* is particularly suited to infect the CF lung.

Thus, the present invention also provides for agents and methods for identifying agents, which inhibit or suppress the isolated *Pseudomonas aeruginosa* factor or Cif protein described herein. Such agents can be identified routinely by those skilled in the art based upon methodologies described herein for measuring CFTR expression in the presence of *Pseudomonas aeruginosa* or the isolated *Pseudomonas aeruginosa* factor or Cif protein. Inhibition of CFTR expression in cells in the presence of *Pseudomonas aeruginosa* or the isolated *Pseudomonas aeruginosa* factor or Cif protein can be measured as described herein in the presence and absence of a test agent. An increase in CFTR expression in the presence of a test agent is indicative of the agent being an inhibitor of suppression of CFTR expression by *Pseudomonas aeruginosa* or the isolated *Pseudomonas aeruginosa* factor.

The present invention also provides methods for inhibiting suppression of CFTR expression resulting from infection by *Pseudomonas aeruginosa*. In these methods, cells infected by *Pseudomonas aeruginosa* are administered an agent which inhibits the isolated factor of *Pseudomonas aeruginosa* or the Cif protein described herein and its suppression of CFTR expression.

Examples of such agents include, but are in no way limited to, compounds which bind to the isolated factor of *Pseudomonas aeruginosa* or Cif protein thereby preventing it from suppressing CFTR expression such as ligands and antibodies and agents which decrease levels of the isolated factor of *Pseudomonas aeruginosa* or Cif protein such as antisense agents or targeted ribozymes.

This present invention also provides methods for inhibiting the epoxide hydrolase activity of PA2934. In these methods, the colorimetric assay for PA2934 activity is used to identify agents that reduce epoxide hydrolase activity.

Examples of such agents include, but are in no way limited to, compounds that bind to the isolated factor of *Pseudomonas aeruginosa* or Cif protein thereby reducing or eliminating epoxide hydrolase activity.

Agents which inhibit the isolated *Pseudomonas aeruginosa* factor or Cif protein identified herein are expected to be useful in pharmacologic suppression of the effect of *P. aeruginosa* on CFTR. Thus, such agents are expected to be useful in treatment and/or alleviation of symptoms of subjects suffering from cystic fibrosis. These agents can be administered alone, or more preferably in combination with known therapies which: (1) promote CFTR exit from the endoplasmic reticulum, (2) activate CFTR in the apical plasma membrane, and/or (3) increase the half-life of CFTR in the apical membrane. By "in combination" it is meant that the agent is administered either simultaneously, before or after the other therapy for cystic fibrosis.

Further, much of the focus in the area of CF therapeutics has centered on discovering compounds capable of increasing apical membrane expression of the ΔF508-CFTR protein. The rationale underlying such a strategy is that increased CFTR activity and increased Cl⁻ ion secretion would result in decreased mucous viscosity, increased mucocilliary clearance and resolution of infections and symptoms. As shown herein, however, in the presence of *P. aeruginosa*, as is the case for the majority of CF patients, this treatment course might be ineffectual as any increase in ΔF508-CFTR protein is reversed due to the activity of Cif. Thus, therapeutic regimes for CF attempting to increase apical membrane expression of ΔF508 should be coupled to either an anti-pseudomonas regimen of antibiotics or compounds specifically targeted to Cif function.

Agents which inhibit the isolated *Pseudomonas aeruginosa* factor or Cif protein identified herein can be administered by various routes including, but in no way limited to, intravenously, intramuscularly, intraperitoneally, via inhalation, intranasally, intrabucally, and orally. Formulations comprising these agents can be prepared using well known techniques selected routinely by the skilled artisan in accordance with the route of administration.

The studies above indicate that CIF reduces the plasma membrane expression of P-glycoprotein (i.e. Pgp or multidrug resistance protein (MDR)), MRP2, BCRP and other members of the ABC transmembrane protein family, whose functions include the transport of small molecules across cell membranes. More specifically, members of the ABC transporter family function by preventing therapeutics including but not limited to anti-cancer therapies and antibiotics from accumulating in the central nervous system, and by conferring the observed "drug resistance" of numerous cancers. To test whether purified PA2934 was necessary and sufficient for reducing the apical membrane expression of the MDCK cell line expressing MDR1, and thus increase the susceptibility of this cell line to the anti-cancer agent Dox, purified PA2934-His or buffer control, was applied to the apical face of MDCK-GPF-MDR1 cells, (Biochem J 2001 355:617-624), incubated for 60 min, then these cells were treated with 0, 1, 3, 5 or 10 μM Dox for 4 hrs at 37 C. While cell viability was reduced at 4 hr by ~5% by treatment with buffer, pre-treatment with PA2934-His resulted in a reduction in viability of ~25%, indicating that treatment with PA2934-His increased susceptibility of the MDR-expressing cells to treatment with this anti-cancer therapeutic.

The following nonlimiting examples are provided to further illustrate the present invention.

EXAMPLES

Example 1

Cell Lines and Cell Culture

Two human cell lines endogenously expressing CFTR, Pgp, MRP1, BCRP and MRP2: (1) Calu-3, an airway epithelial cell line and (2) Caco-2, an intestinal epithelial cell line, were used as a model of polarized epithelial cells. Studies were also conducted in polarized human CFBE41o– cells and Madin Darby Canine Kidney (MDCK) cells stably expressing wild-type (wt)-CFTR, and in MDCK cells stably expressing Pgp.

Epithelial cell cultures were grown on Transwell permeable growth supports (24 mm diameter, 0.4 μm pore size; Corning Corporation, Corning, N.Y.: #3412). Apical membrane expression of CFTR, Pgp, MRP1, BCRP and MRP2 was measured by cell-surface biotinylation as described by Lisanti, et al. (J. Cell Biol. 1989 109:2117-2127) and Swiatecka-Urban et al. J. Biol. Chem. 2002 277(42):40099-105).

Calu-3 cells obtained from the American Type Culture Collection (Manassas, Va.) were maintained in MEM containing 50 U/ml penicillin, 50 μg/ml streptomycin, 2 mM L-glutamine, 1 mM sodium pyruvate, and 10% FBS in a 5% $CO_2$/95% air incubator at 37° C. Calu-3 cells were seeded on Transwell permeable supports ($1\times10^6$ on 6.5 mm and $4\times10^6$ on 24 mm diameter, 0.4 μm pore size; Corning Corporation; Corning, N.Y.) coated with Vitrogen plating medium (VPM) containing DMEM (JRH Biosciences; Lenexa, Kans.), human fibronectin (10 μg/ml; Collaborative Biomedical Products; Bedford, Mass.), 1% Vitrogen 100 (Collagen; Palo Alto, Calif.), and BSA (10 μg/ml; Sigma-Aldrich; St. Louis, Mo.). Cells were grown in air-liquid interface culture at 37° C. for 14 to 21 days. Under these conditions, Calu-3 cells become polarized.

CFBE41o– parental cells (ΔF508/ΔF508), and CFBE41o– cells stably expressing either wt-CFTR or ΔF508-CFTR were maintained in MEM supplemented with 50 U/ml penicillin, 50 μg/ml streptomycin, 2 mM L-glutamine, 10% FBS, and 1 μg/ml blasticidine (wt-CFTR) or 2 μg/ml puromycin (F508-CFTR) in a 5% $CO_2$/95% air incubator at 37° C. CFBE41o– cells were seeded on 12 mm Snapwell or 24 mm Transwell permeable supports (0.4 μm pore size; Corning Corporation; Corning, N.Y.) at $1\times10^6$ and grown in air-liquid interface culture at 37° C. for 6-9 days and at 27° C. for 36 hours to increase trafficking and expression of ΔF508-CFTR in the apical membrane. Under these conditions, CFBE41o– cells form polarized monolayers.

MDCK cells stably expressing GFP-wt-CFTR or GFP-ΔF508-CFTR fusion proteins were established and maintained in culture in a 5% $CO_2$/95% air incubator at 37° C. in MEM complete medium containing 50 U/ml penicillin, 50 μg/ml streptomycin, 2 mM L-glutamine, 10% FBS, and 150 μg/ml G418. Addition of GFP to the N-terminus of CFTR has no effect on CFTR localization, trafficking, function as a Cl channel, or on its degradation. MDCK cells were seeded on Transwell permeable supports ($0.2\times10^6$ on 6.5 mm and 24 mm diameter, 0.4 μm pore size; Corning Corporation; Corning, N.Y.) and grown in culture at 37° C. for 7-10 days. Under these conditions, MDCK cells become polarized. Sodium butyrate (5 mM; Sigma-Aldrich; St. Louis, Mo.) was added to the MDCK cell culture medium 16-18 hours before experiments to stimulate CFTR expression.

Parental human bronchial epithelial CFBE41o⁻ cells (ΔF508/ΔF508), originally immortalized and characterized by Gruenert and colleagues (Bruscia et al. Gene Ther 2002 9:683-685; Cozens et al. Am J Respir Cell Mol Biol 1994 10:38-47), were stably transduced with WT-CFTR (WT-CFBE cells) (Bebok, et al. J Physiol (Lond) 2005 569:601-615). WT-CFBE cells were cultured in a 5% $CO_2$-95% air incubator at 37° C. as previously described (48). To establish polarized monolayers, $1\times10^6$ CFBE41o– cells were seeded onto 12-mm Snapwell or 24-mm Transwell permeable supports (0.4-μm-pore size; Corning) and grown in an air-liquid interface culture at 37° C. for 7-9 days.

Example 2

P. aeruginosa Isolates for Studies on Apical Membrane Expression in Epithelial Cells A recent clinical isolate of *P. aeruginosa* strain PA14 as well as eight clinical isolates from hospitalized patients were used to study the effects on apical membrane expression of ABC transporters in epithelial cells. Eighteen-hour PA14 cultures in Lurie Bertani (LB) media were centrifuged and the pelleted bacteria were washed and resuspended in Phosphate Buffered Saline (PBS) at $5\times10^9$ Colony Forming Units (CFU)/ml. The non-pelleted fraction of the PA14 cultures or the cell-free bacterial filtrates containing factors secreted by *P. aeruginosa* were used in separate experiments.

Example 3

*P. aeruginosa* Cultures for Studies of CFTR Expression in Cystic Fibrosis Patients Lysogeny broth (5 ml) was inoculated with *P. aeruginosa* strain UCBPP-PA14 (PA14), a relatively recent laboratory isolate from a burn patient, from a glycerol stock and incubated at 37° C. with rotation until the bacterial count reached OD=1.5 corresponding to a bacterial count of $5 \times 10^9$ CFU/ml (14-18 hours of culture). Bacteria were harvested by centrifuging cultures at 4800×g for 10 minutes at 4° C. Subsequently, after washing with PBS, pH 7.4 at 4° C. to eliminate factors secreted into the extracellular environment, the bacteria were resuspended in PBS to a stock concentration of $5 \times 10^9$ CFU/ml. In addition, 12 clinical isolates of *P. aeruginosa*, 6 from cystic fibrosis and another 6 from non-cystic fibrosis patients, were cultured as described above. Heat-killed bacteria, used as a control, were prepared by incubating the PBS-resuspended cultures at 95° C. for 10 minutes.

Bacteria-free *P. aeruginosa* filtrates were prepared by centrifugation of bacterial cultures, grown as described above, at 4800×g for 10 minutes at 4° C. Supernatants were harvested and filter-sterilized at 4° C. using a 0.2 µm filter resulting in bacteria-free filtrates. Heat-inactivated filtrates, used as control, were prepared by incubating the filtrates at 60° C. for 45 minutes.

Example 4

Measurement of Apical Membrane Expression of ABC Transporter in the Presence of *P. aeruginosa* Factor In these experiments, apical membrane proteins were biotinylated at 4° C. using a derivative of biotin (EZ-Link™ Sulfo-NHS-LC-Biotin: Pierce). Subsequently, apical membranes in epithelial cells were incubated with washed *P. aeruginosa* strain PA14 or with cell-free PA14 filtrate at 37° C. Heat-killed PA14 (10 minutes at 90° C.), heat-inactivated PA14 filtrates (10 minutes at 60° C.), and vehicle alone (PBS or LB media) were used as control. Subsequently, cells were lysed, biotinylated proteins were isolated by streptavidin-agarose beads, eluted into SDS-sample buffer, and separated by 7.5% SDS-PAGE. Biotinylated CFTR, Pgp, BCRP and MRP-2 were analyzed by Western blotting using antibodies against CFTR, Pgp, and MRP-2, respectively. Ussing chamber studies that measure CFTR-mediated chloride currents were performed to provide additional, functional support for the view that PA14 reduced the plasma membrane expression of CFTR as described by Vandorpe et al. (Am. J. Physiol. Cell Physiol. 1995 269(38):C683-689).

Example 5

Ussing Chamber Measurements

Monolayers grown on Transwell (6.5 mm diameter) or Snapwell (12 mm diameter) permeable supports, as described in Example 1, were mounted in an Ussing-type chamber (Jim's Instruments; Iowa City, Iowa or Physiologic Instruments; San Diego, Calif.) and bathed in solutions, pH 7.4 maintained at 37° C. and stirred by bubbling with 5% $CO_2$/95% air. Short circuit current (Isc) was measured by voltage-clamping the transepithelial voltage across the monolayers to 0 mV with a voltage clamp (model VCC MC6, Physiologic Instruments, San Diego, Calif.). Current output from the clamp was digitized by an analog-to-digital converter (iWorx; Dover, N.H.). Data collection and analysis were done with LabScribe v1.6 Software (iWorx; Dover, N.H.). Stimulated Isc was measured after addition of 100 µM CPT-cAMP (Calu-3 and MDCK cells) or 20 µM forskolin (wt-CFTR CFBE41o– cells) to the apical and basolateral bath solution or 50 µM genistein (ΔF508-CFTR CFBE41o– cells) to the apical bath solution. Net stimulated Isc (ΔIsc) was calculated by subtracting the baseline Isc measured before stimulation from the peak Isc measured after stimulation. Glybenclamide (200 µM) was added to the apical bath solution to inhibit CFTR-mediated Isc.

Intact Calu-3 monolayers were bathed in MEM (–FBS). In order to determine the effects of PA14 on CFTR-mediated Cl currents across the apical membrane of Calu-3 cells, basolateral membranes were permeabilized with nystatin (200 µg/ml) and an apical-to-basolateral Cl– concentration gradient was established. A low Cl–, high-Na+, high-gluconate, basolateral bath solution was used to prevent cell swelling due to the increased basolateral Cl– permeability under these conditions. The basolateral bath solution contained (in mM) 115Na-gluconate, 5NaCl, 25$NaHCO_3$, 3.3$KH_2PO_4$, 0.8$K_2HPO_4$, 1.2$MgCl_2$, 1.2 $CaCl_2$, 10 glucose. The apical bath solution contained (in mM) 120 NaCl, 25$NaHCO_3$, 3.3$KH_2PO_4$, 0.8$K_2HPO_4$, 1.2$MgCl_2$, 1.2$CaCl_2$, mannitol. Mannitol was substituted for glucose in the apical bath solution to eliminate the contribution of the Na-glucose cotransporter to Isc. Successful permeabilization of the basolateral membrane was based upon the recording of a current consistent with the apical-to basolateral flow of negative charge. CFBE41o– cells were bathed in solutions with a basolateral-to-apical Cl– gradient in the presence of amiloride (100 µM) in the apical bath solution to inhibit Na+ absorption through the epithelial Na+ channel (ENaC). The apical bath solution contained (in mM) 115Na-gluconate, 5NaCl, 25$NaHCO_3$, 3.3$KH_2PO_4$, 0.8$K_2HPO_4$, 1.2$MgCl_2$, 4Ca gluconate, 10 mannitol. The basolateral bath solution contained (in mM) 120 NaCl, 25$NaHCO_3$, 3.3$KH_2PO_4$, 0.8$K_2HPO_4$, 1.2$MgCl_2$, 1.2$CaCl_2$, 10 glucose. MDCK monolayers were bathed in MEM solution in the presence of amiloride (100 µM) in the apical bath solution to inhibit Na+ absorption through ENaC.

To determine the effects of purified, recombinant PA2934 on the CFTR-mediated Cl⁻ current ($I_{sc}$), forskolin (20 µM) was added to the apical and basolateral solutions to stimulate $I_{sc}$ and then 50 µg of purified PA2934-His in buffer or buffer alone (20 mM HEPES buffer, pH 7.5 containing 500 mM NaCl) was added to the apical bath solution. An equal volume of buffer was also added to the basolateral side to maintain the apical-to-basolateral Cl⁻ concentration gradient. $CFTR_{inh}$-172 (5 µM), a known inhibitor of CFTR activity (Ma et al. J Clin Invest 2002 110:1651-1658), was added to apical solution as a positive control for inhibition of CFTR Cl channels. $I_{sc}$ data are expressed as the change in forskolin stimulated $I_{sc}$.

Example 6

Antibodies

Antibodies used were monoclonal anti-gp114 antibody (Brändli A W, at al. J Cell Biol 1990 111:2909-2921; Verkade P, et al. J Cell Biol 2000 148: 727-739.), monoclonal anti-human CFTR C-terminus, clone 24-1 (R&D Systems; Minneapolis, Minn.), monoclonal anti-CFTR, clone M3A7 (Upstate Biotechnology; Lake Placid, N.Y.), monoclonal anti- GFP JL-8 (BD Biosciences; San Jose, Calif.), monoclonal anti-transferrin receptor (Zymed; San Francisco, Calif.), monoclonal anti-Na,K-ATPase (Upstate Biotechnology; Lake Placid, N.Y.), and goat anti-mouse and goat anti-rabbit HRP secondary antibodies (BioRad Laboratories; Hercules, Calif.). All purchased antibodies were used at the concentrations recommended by the manufacturer.

Polyclonal rabbit anti-Cif antibodies were produced by Covance Research Products (Denver, Pa.). Briefly, purified penta-histidine tagged Cif was purified as described above using nickel-affinity chromatography and diluted to a final concentration of 1 mg/ml. Purified protein was then provided to Covance Research Products for immunizations. Serum from Day 51 bleeds were used at 1:1000 using standard western blotting techniques as described by Caiazza, N. C. and G. A. O'Toole (J. Bacteriol 2004 186:4476-4485).

Antibody to the outer membrane (OM) protein OprF was produced against a partially purified OM fraction of *P. aeruginosa*. Specific cross-reactivity to the OprF protein was determined in two ways. First, vesicles were prepared using the Optiprep gradient described above. The gradient fraction shown previously to contain the suspected OprF cross-reacting band was TCA precipitated, the proteins resolved by SDS page, a gel slice corresponding to ~37 kDa was excised and analyzed by mass spectroscopy. Five peptides matching OprF were identified in this sample. Second, the loss of cross-reacting band of the appropriate size (~37 kDa) was observed in an oprF mutant strain.

Example 7

Cell Surface Biotinylation, Endocytic Assay and Endocytic Recycling Assay

Cell surface biotinylation, endocytic assays, and endocytic recycling assays were performed on polarized epithelial cells grown on Transwell permeable supports (24 mm diameter, 0.4 μm pore size; Corning Corporation; Corning, N.Y.). Sodium butyrate (5 mM) was used to stimulate CFTR expression in Calu-3 and MDCK cells. The temperature in the incubator was reduced (27 C) to increase apical membrane expression of ΔF508-CFTR in CFBE41o– cells.

Example 8

Bacterial Strains, Media and Chemicals

Bacterial strains and plasmids used in experiments described herein are shown in Table 1.

| Strain or plasmid | Relevant genotype |
|---|---|
| *P. aeruginosa* PA14 | Wild Type[a] |
| SMC3498 | PA14 PA2934 single crossover mutant |
| SMC3499 | PA14 PA4476 single crossover mutant |
| SMC3500 | PA14 PA1914 single crossover mutant |
| SMC3501 | PA14 + pMQ70 |
| SMC3502 | PA14 ΔPA2934 |
| SMC3503 | SMC3502 + pDPM73 (2934-His) |
| SMC3504 | SMC3502 + pMQ70 |
| SMC3505 | *E. coli* Top10 + pDPM73(PA2934-His) |
| SMC3506 | SMC3498 + pDPM73(PA2934-His) |
| SMC3507 | *E. coli* Top10 + pDPM77 (PA2934-His, H269A) |
| SMC3510 | *E. coli* S17 + pDPM74 |
| SMC1584 | *P. aeruginosa* clinical isolate, non-mucoid |
| SMC1585 | *P. aeruginosa* clinical isolate, mucoid |
| SMC1586 | *P. aeruginosa* clinical isolate, non-mucoid |
| SMC1587 | *P. aeruginosa* clinical isolate, mucoid |
| SMC1588 | *P. aeruginosa* clinical isolate, non-mucoid |
| SMC1589 | *P. aeruginosa* clinical isolate, mucoid |
| SMC1590 | *P. aeruginosa* clinical isolate, mucoid |
| SMC1591 | *P. aeruginosa* clinical isolate, non-mucoid |
| SMC1593 | *P. aeruginosa* clinical isolate, non-mucoid |
| SMC1596 | *P. aeruginosa* clinical isolate, mucoid |
| *E. coli* Top10[b] | F-mcrA Δ(mrr-hsdRMS-mcrBC) |
| *S. cerevisiae* | Δ80lacZDM15 ΔlacX74 recA1 araΔ139 Δ(araleu)7697 galU galK rpsL (Str$^R$) endA1 nupG |
| INVSc1[b] | MATa his3D1 leu2 trp1-289 ura3-52 MAT his3D1 leu2 trp1-289 ura3-52 |
| Plasmids | |
| pDPM60 | PA2934 fragment in pMQ89 Gm$^r$ |
| pDPM61 | PA4476 fragment in pMQ89, Gm$^r$ |
| pDPM66 | PA1914 fragment in pMQ89, Gm$^r$ |
| pDPM70 | WT PA2934 in pMQ71, Cb$^r$ Ap$^r$ |
| pDPM73 | PA2934 histidine fusion in pMQ70 Cb$^r$ Ap$^r$ |
| pDPM74 | PA2934 in-frame deletion plasmid Gm$^r$ |
| pDPM77 | Derivative of pDPM73 carrying H269A mutation |
| pMQ30[c] | *P. aeruginosa* suicide vector for clean deletions. Gm$^r$ |
| pMQ89[c] | Single crossover mutation vector Gm$^r$ |
| pMQ70[c] | Arabinose inducible expression vector Cb$^r$ Ap$^r$ URA3 |

[a]described by Rahme et al. Science 1995. 268: 1899.
[b]purchased from Invitrogen
[c]described by Shanks et al. Appl. Environ. Microbiol. 2006. 72: 5027.

All bacterial strains were grown in lysogeny broth (LB) unless otherwise noted. Growth media was supplemented with antibiotics at the following concentrations; gentamycin, 10 μg/ml (*Escherichia coli*), 100 μg/ml (*P. aeruginosa*); Ampicillin, 150 μg/ml (*E. coli*), 1.5 μg/ml (*P. aeruginosa*). All strains were grown at 37° C. Yeast cultures were grown in either rich (YPD) or minimal media (SD-Ura) (Sunrise Science Products, San Diego, Calif.) at 30° C. All restriction enzymes were purchased from New England Biolabs (Beverly, Mass.). All plasmids were constructed in *E. coli* Top10 using standard protocols or *Sacharomyces cerevisae* Inv-Sc (Invitrogen, Carlsbad, Calif.) using in vivo recombination, and electroporated or conjugated into *P. aeruginosa* strain PA14 as described by Choi et al. (J Microbiol Methods 2006 64:391-397) and Shanks et al. (Appl Environ Microbiol 2006 72:5027-5036).

Example 9

Purification of CIF

Cultures of *P. aeruginosa* PA14 (5 ml) were grown overnight at 37° C. followed by a 1:1000 dilution into 100 ml LB. Cultures were grown with shaking at 37° C. for 18 hours. Supernatant was harvested by centrifugation at 7000×g for 15 minutes followed by filtration through a 0.22 μm filter. Sterile supernatants were concentrated 10-fold using Amicon Centriprep centifugation filters as per manufacturer's instructions (Millipore, Billerica, Mass.). Concentrated supernatants were dialyzed against 4 liters of 25 mM MES buffer pH 6.5 for 2 hours using Pierce Slide-a-lyzers, 10 kDa cutoff (Pierce, Rockford, Ill.). Samples were then fractionated utilizing a 1 ml Amersham Biosciences HiTrap Q FF anion exchange chromatography column (Uppsala, Sweden) using a stepwise gradient or 0, 50 mM and 2M NaCl. Collected fractions were then dialyzed against 4 liters of phosphate buffered saline (PBS) and utilized in apical CFTR membrane expression assays described below.

Example 10

Multidimensional Protein Identification Technology (MuDPIT) Analysis of Active Fractions Samples for MudPIT analysis were lyophilized using a Savant SC110 Speed-Vac and stored on ice. Samples were submitted to the Keck Proteomics and Mass Spectrometry facility at Yale University for MudPIT analysis. The resulting data was analyzed utilizing Mascot and Seaquest softwares and ion masses were compared to the available *P. aeruginosa* PA14 protein database (NCBI nr 20040730). MudPIT separates proteins using columns consisting of strong cation exchange (SCX) resin in series with reverse phase (RP) resin. Through cycles of increasing salt and hydrophobicity, peptides are eluted from tandem column resulting in high resolution of the peptides. The mass spectrometer isolates peptides as they elute and subjects them to Collision-Induced Dissociation, recording the fragment ions in a tandem mass spectrum. These spectra are matched to database peptide sequences using the SEQUEST algorithm.

Example 11

Determination of CFTR Expression in the Apical Plasma Membrane

To identify active fractions during CIF purification, as well as to assay CIF activity of various strains and with purified protein, the surface biotinylation assay described in Example 4 was used. In these surface biotinylation experiments, unless otherwise noted, 50 μg of purified PA2934-His was used in all.

Example 12

Molecular Techniques

All molecular techniques were performed in accordance with procedures described by Rommens et al. (Science 1989 245:1059-1065). Single crossover mutations of PA1914, PA2934 and PA4476 were performed utilizing suicide plasmids based on pMQ89 as described by Shanks et al. (Appl Environ Microbiol 2006 72:5027-5036). The deletion of the PA2934 gene was constructed as described by Kuchma et al. (J Bacteriol 2005 187:1441-1454). Plasmids were propagated in *E. coli* S17 and conjugated into *P. aeruginosa* strain PA14 as described by Caiazza, N. C. and O'Toole, G. A. (J Bacteriol 2004 186:4476-4485). Recombinant strains were selected for and maintained in media supplemented with gentamycin.

Example 13

Plasmid Construction

Plasmids pDPM60, pDPM61 and pDPM66 contain an approximate 400 by internal region of PA2934, PA4476 and PA1914, respectively. The following primers were used to amplify the internal region of PA2934, PA4476 and PA1914; PA2934_SXO_for, PA2934_SXO_rev, PA4476_SXO_for, PA4476_SXO_rev, PA1914_SXO_for, and PA1914_SXO_rev. Primers were engineered to create an amplicon that could be digested with EcoRI and HindIII and ligated into the suicide vector pMQ89 digested in a similar manner.

Construction of the PA2934 deletion plasmid was performed as described by Shanks et al. (Appl Environ Microbiol 2006 72:5027-5036) using primers PA2934_KO_1, PA2934_KO_2, PA2934_KO_3, and PA2934_KO_4. Amplicons were created using primer pairs KO_1 and KO_2, and KO_3 and KO_4, and were recombined using *S. cerevisiae* InvSc1 (Invitrogen) into plasmid pMQ30 linearized with restriction enzymes EcoRI, HindIII and BamHI.

Plasmid pDPM70, containing the full length WT PA2934 ORF was constructed by amplifying PA2934 with primers PA2934 comp for and PA2934 comp rev followed by digestion with EcoRI and NheI. The digested amplicon was ligated into pMQ70 as described by previously digested in a similar manner. pDPM73 was created utilizing in vivo recombination cloning as described by Shanks et al. (Appl Environ Microbiol 2006 72:5027-5036) utilizing pDPM70 digested with NheI and primer PDPM70-His resulting in an in-frame, C-terminal penta-histidine tag fusion to the PA2934 protein. Plasmid pDPM77, which expresses the PA2934-His protein with a H269A mutation, was constructed using a similar technique. The PA2934 open reading frame was amplified from pDPM73 using primer pairs PA2934 mut out for and H269A_rev and H269A for and PA2934 mut out rev. The resulting amplicons were utilized in the in vivo recombination cloning technique utilizing linearized pMQ70 as the plasmid backbone.

| Primers | Primer sequence | SEQ ID NO: |
|---|---|---|
| PA2934_SXO_for | 5'-GAGGAATTCCCCGTCCCGAATGGCTTCG-3' | 3 |
| PA2934_SXO_rev | 5'-CCGCGGATCCGCCAGACCAGCGACTCGCCCTGGGCG-3' | 4 |
| PA4476_SXO_for | 5'-CCGCGGATCCGTCCTGGGTCTGTGCGCCCTGGTACTGG-3' | 5 |
| PA4476_SXO_rev | 5'-CCGCGAATTCCGCGCCGACCGCGCTGAGCGACAGCG-3' | 6 |
| PA1914_SXO_for | 5'-CGCCGGATCCGGCCTGGCGCTGACACCCGCGGCCC-3' | 7 |
| PA1914_SXO_rev | 5'-CCGCGAATTCGCACTGCCGCGAATGGTCGCCGCGG-3' | 8 |
| PA2934_KO_1 | 5'GGGTTTTCCCAGTCACGACGTTGTAAAACGACGGCCAGTGCC CGCAAGCGGCTGTTCGTCGCCTGCC-3' | 9 |

-continued

| Primers | Primer sequence | SEQ ID NO: |
|---|---|---|
| PA2934_KO_2 | 5'-CTGATCGCCCGGACCGGGACGACGGTTGTGCTTCCT TGGTGGGGTC-3' | 10 |
| PA2934_KO_3 | 5'-GACCCCACCAAGGAAGCACAACCGTCGTCCCGGTCC GGGCGATCAG-3' | 11 |
| PA2934_KO_4 | 5'-GTGAGCGGATAACAATTTCACACAGGAAACAGCTAT GACCCGAACAGCGCGGTGTCCTTGAAGC-3' | 12 |
| PA2934_comp_for | 5'-CCGCGCTAGCCCAAGGAAGCACAACCATGATCC-3' | 13 |
| PA2934_comp_rev | 5'-CCGCGGTACCTCAGCGACCGCGGCTGAGGAAG-3' | 14 |
| PDPM70-His | 5'-GTATCAGGCTGAAAATCTTCTCTCATCCGCCTCAATG ATGATGATGATGGCGACCGCGGCTGAGGAAGTCGATC ACCAGG-3' | 15 |
| PA2934_mut_out_for | 5'-GATTTAATCTGTATCAGGCTGAAAATCTTCTCTCATC CGCCTCAATGATGATGATGATGATGGCG-3' | 16 |
| H269A_rev | 5'-CCATGACCCTCGCCGGCGGCGGCGCCGGCGGCATGGG CACGTTCCAGCTGG-3' | 17 |
| H269A_for | 5'-CCAGCTGGAACGTGCCCATGCCGCCGGCGCCGCCGCC GGCGAGGGTCATGG-3' | 18 |
| PA2934_mut_out_rev | 5'-CCATGACCCTCGCCGGCGGCGGCGCCGGCGGCATGG GCACGTTCCAGCTGG-3' | 19 |
| PA2934_rt_1 | 5'-CTCCTGGCCGGCATCGCCCTGACCTTCTCC-3' | 20 |
| PA2934_rt_2 | 5'-CCATTCGTACCAGGTCTGGCCGAAGCCGTGC-3' | 21 |
| Rp1U_rt_1 | 5'-GGTGGCAAGCAGCACAAAGTCACCG-3' | 22 |
| Rp1U_rt_2 | 5'-GCGGACCTTGTCGTGACGGCCGTGG-3' | 23 |

Example 14

Purification of PA2934-His Protein

Strain SMC3505, E. coli Top10 expressing a C-terminal penta-histidine variant of PA2934 (PA2934-His) from plasmid pDPM73 was grown overnight at 37° C. under selection. Cultures were diluted 1:100 in 4 liters of LB media supplemented with ampicillin and 0.2% arabinose and grown for 8 hours at 37° C. with shaking. Following growth, culture supernatant was harvested by centrifugation of bacteria at 7000×g for 20 minutes. Supernatants were filtered through a 0.22 µm filter to remove any bacteria remaining in suspension. Sterile supernatant was then fractionated utilizing an Amersham HisTrap FF 5 ml Nickel affinity column. Protein was eluted over a 20-500 mM imidazole gradient with the bulk of the purified PA2934-His eluting at approximately 100 mM. Fractions containing the protein were concentrated using an Amicon Ultra 15 centrifugation filter with a cutoff of 30 kDa as per manufacturers instructions followed by dialysis against 20 mM HEPES buffer pH 7.5 containing 500 mM NaCl. Protein concentration was determined utilizing the Biorad protein assay kit (Hercules, Calif.). Purity was determined by resolving sample by SDS-PAGE and detection by Coommasie blue staining.

Example 15

Epoxide Hydrolase Activity Assay

Purified PA2934-His was assayed for its ability to degrade the epoxide hydrolase synthetic substrate (2S,3S)-trans-3-Phenyl-2-oxiranylmethyl 4-nitrophenyl carbonate ((S)-NEPC) (Sigma, St. Louis, Mo.). PA2934-His was incubated in 20 mM Tris pH 8.4, 500 mM NaCl with 100 M (S)-NEPC at a final volume of 200 µL at 37° C. for 6 hours. Degradation of (S)-NEPC was measured as an increase in absorbance at $OD_{405}$ utilizing a Molecular Devices SpectraMax M2 plate reader. Reactions were normalized to controls lacking enzyme, accounting for spontaneous hydrolysis of the substrate.

Example 16

RNA Purification from Bacterial Cells and cDNA Synthesis

Strains for quantitative real time reverse transcription polymerase chain reaction (qRT-PCR) were grown overnight in LB medium and subsequently diluted 1:100 in LB medium and grown to $OD_{600}$ of 2.5. Cultures (500 µl) were harvested and centrifuged at 16,000×g for two minutes and the cell pellets were frozen at −80° C. Strains were grown in triplicate and two samples were harvested per replicate. RNA was isolated using the Qiagen RNeasy kit as per manufacturer's instructions. Following initial purification, samples were incubated with RNase free DNase for 1 hour at 37° C. to further remove contaminating DNA and re-purified using the Qiagen RNeasy kit. DNA contamination was assessed by using samples in a standard PCR assay. RNA concentration was determined using a Nanodrop ND-1000 spectrophotometer (Wilmington, Del.). cDNA was amplified utilizing Superscript III First Strand Polymerase kit (Invitrogen, Carlsbad, Calif.) per manufacturer's instructions utilizing random hexamers to prime the reactions. One microgram of RNA was used for cDNA synthesis.

Example 17

RNA Purification from Sputum and cDNA Synthesis

Respiratory sputum was collected from two individuals with Cystic Fibrosis and divided such that one sample was subjected to clinical microbiological analysis while the other was used for the purposes of RNA isolation. All sputum samples contained P. aeruginosa based on microbiological culture analysis in the DHMC clinical laboratory. After collection, an equal volume of RNALater, an RNA stabilizing agent, was added to each sample prior to storage at −80° C. To isolate total sputum RNA, samples were thawed on ice, and centrifuged for 10 minutes at 13,000 rpm. The pellet was resuspended, followed by homogenization by passage through a 24 gauge syringe needle several times. Subsequent RNA purification steps were performed with the Qiagen Rneasy kit according to the manufacturer's protocols. Contaminating DNA was removed using the Ambion DnaseFree kit according to manufacturer's instructions. The RNA was analyzed spectraphotometrically to determine concentration, and the absence of DNA was assessed by real-time reverse transcriptase PCR analysis. For cDNA synthesis, 500 ng of RNA was used as the template in a cDNA synthesis reaction with Superscript III using random primers $(NS)_5$ according to the manufacturer's instructions; no RT controls were included in all analyses.

Example 18 qRT-PCR

Quantitative reverse transcription polymerase chain reactions (qRT-PCR) were carried out in accordance with the procedure of Kuchma et al. (J Bacteriol 2005 187:1441-1454). Primers were engineered to amplify the first 100 base pairs of the PA2934 open reading frame. The rplU gene served as a control for all qRT-PCR reactions as previous reports have demonstrated that transcription is independent of growth stage or conditions across all P. aeruginosa strains assayed to date (Kuchma et al. J Bacteriol 2005 187:1441-1454; Mah et al. Nature 2003 426:306-31032). All qRT-PCR reactions were performed using an ABI 7500 Real Time PCR System (Applied Biosystems, Foster City, Calif.).

Example 19

Vesicle Fractionation

Vesicles were purified from an overnight culture of P. aeruginosa PA14 grown to stationary phase using one of the following methods. Cells were removed by centrifugation and supernatants were filtered through a 0.22 μm filter, followed by centrifugation at 39,000×g for 1 hour at 4° C. Pellets from centrifugation were resuspended in 50 mM HEPES buffer, pH 6.8, and adjusted to 45% Optiprep in 10 mM HEPES containing 0.85% NaCl, pH 7.4 (weight/volume). Discontinuous Optiprep gradients were then layered over the vesicles samples as follows: 0.8 ml of 40%, 0.8 ml 35%, 1.6 ml 30%, 0.8 ml 20% of Optiprep in 10 mM HEPES/0.85% NaCl buffer. Gradients were centrifuged at 100,000×g for 18 hours at 4° C. Immediately following centrifugation, 500 μl fractions were collected from gradients. Proteins in each fraction were precipitated with 10% TCA and visualized with 12% SDS-PAGE and Coomassie staining.

Alternatively, cells were removed by centrifugation and supernatants were filtered through a 0.45 μm filter, followed by concentrating the sample with an Amicon ultra 15, 30 kDa cutoff membrane filter centrifuged at 4000×g for 15 minutes. The filtered supernatant at 45,000×g for 1 hour and the pellet resuspended in 4 ml of 20 mM HEPES, pH 7.4 plus 500 mM NaCl followed by a second centrifugation at 45,000×g for 1 hour and the pellet again resuspended in 4 ml of 20 mM HEPES, pH7.4 plus 500 mM NaCl. 20 μl 1.5% DOC and 200 μl 72% TCA were added to 1 ml of vesicle fraction and incubated on ice for 10 minutes followed by centrifugation at 16,000×g for 15 minutes at RT. The pellet was washed twice with ice cold 70% ethanol, and the residual ethanol evaporated by incubation at 65° C. The pellet was resuspended in 200 μl of 1×SDS running buffer and a 10 μl sample was resolved by SDS-PAGE and Western blotting performed as described by Caiazza and O'Toole. (J Bacteriol 2004 186:4476-4485).

Example 20

Doxorubicin Treatment

MDCK-GFP-MDR1 cells, MDCK-C7 cells stably transfected with GFP-Pgp under the transcriptional control of human MDR1 promoter as described by Maitra et al. (Biochem J 2001 355:617-624) were used in these studies. MDCK-GFP-MDR1 cells were seeded in 96 well plates at approximately 5000 cells per well, and after 24 hours, the cells were pretreated with purified Cif-His or buffer for 60 minutes. Doxorubicin (Dox, 0-10 μm) was added and incubated for 4 hours at 37° C. Cell viability was then assessed using the CellTiter 96Queous One Solution Cell Proliferation assay. After incubating for 4 hours at 37° C., the absorbance was determined at 490 nm.

Example 21

Data Analysis and Statistics

Each experiment was repeated a minimum of three to six times. Statistical analysis of the data was performed using GraphPad Prism version 4.0 for Macintosh (GraphPad Software; San Diego, Calif.). Means were compared by t-test. A P value <0.05 was considered significant. Data are expressed as mean±SEM.

What is claimed is:

1. A method for modulating plasma membrane expression of an ATP-binding cassette (ABC) transmembrane protein in a cell comprising administering to the cell a composition that modulates plasma membrane expression of ABC transmembrane protein, said composition comprising:

(a) a cystic fibrosis transmembrane conductance regulator inhibitory factor protein of SEQ ID NO:1 or fragment of SEQ ID NO:1 which exhibits the same or similar plasma membrane expression of the ABC transmembrane protein modulating activity as SEQ ID NO:1; and (b) a physiologically acceptable vehicle.

2. The method of claim 1 wherein the cell is a mammalian cell.

3. The method of claim 1 wherein the composition comprises the cystic fibrosis transmembrane conductance regulator inhibitory factor protein of SEQ ID NO:1.

* * * * *